(12) United States Patent
Perera

(10) Patent No.: US 11,081,210 B2
(45) Date of Patent: Aug. 3, 2021

(54) DETECTION OF HUMAN LEUKOCYTE ANTIGEN LOSS OF HETEROZYGOSITY

(71) Applicant: TEMPUS LABS, INC., Chicago, IL (US)

(72) Inventor: Jason Perera, Chicago, IL (US)

(73) Assignee: TEMPUS LABS, INC., Chicago, IL (US)

( * ) Notice: Subject to any disclaimer, the term of this patent is extended or adjusted under 35 U.S.C. 154(b) by 0 days.

(21) Appl. No.: 16/789,413

(22) Filed: Feb. 12, 2020

(65) Prior Publication Data

US 2020/0258597 A1 Aug. 13, 2020

Related U.S. Application Data

(60) Provisional application No. 62/932,090, filed on Nov. 7, 2019, provisional application No. 62/889,510, filed on Aug. 20, 2019, provisional application No. 62/804,501, filed on Feb. 12, 2019.

(51) Int. Cl.
| | |
|---|---|
| *G16B 30/00* | (2019.01) |
| *C12Q 1/6827* | (2018.01) |
| *G16B 50/30* | (2019.01) |
| *G06N 3/00* | (2006.01) |

(52) U.S. Cl.
CPC ........... *G16B 30/00* (2019.02); *C12Q 1/6827* (2013.01); *G06N 3/002* (2013.01); *G16B 50/30* (2019.02); *C12Q 2600/156* (2013.01); *C12Q 2600/172* (2013.01)

(58) Field of Classification Search
CPC ...... G16B 30/00; G16B 50/30; C12Q 1/6827; G06N 3/002
USPC .......................................................... 702/19
See application file for complete search history.

(56) References Cited

FOREIGN PATENT DOCUMENTS

| WO | 2014/116729 A2 | 7/2014 |
|---|---|---|
| WO | 2018/009723 A1 | 1/2018 |
| WO | 2019/012296 A1 | 1/2019 |

OTHER PUBLICATIONS

Abelin et al., Defining HLA-II ligand processing and binding rules with mass spectrometry enhances cancer epitope prediction, Immunity, 51(4):766-779 (2019).
Anagnostou et al., Multimodal genomic features predict outcome of immune checkpoint blockade in non-small-cell lung cancer, Nature Cancer, 1:99-111 (2020).
Chowell et al., Patient HLA class I genotype influences cancer response to checkpoint blockade immunotherapy, Science, 359(6375):582-587 (2018).
Conway et al., Genomics of response to immune checkpoint therapies for cancer: implications for precision medicine, Genome Medicine, 10:93 (2018).
Doran et al., T-Cell receptor gene therapy for human papillomavirus-associated epithelial cancers: A First-in-Human, Phase I/II Study, J. Clin. Oncol., 37(30):2759-2768 (2019).
ImmunoID NeXT, The Universal Cancer Immunogenomics Platform, Advancing Modern Precision Oncology, Personalis, available online at < https://www.personalis.com/immunoid-next-platform/ >, 2020, 9 pages.
Lee et al., Kourami: graph-guided assembly for novel human leukocyte antigen allele discovery, Genome Biology, 16 (2018).
Loo et al., Allele-specific copy number analysis of tumors, PNAS, 107(39):16910-16915 (2010).
Masuda et al., Loss or down-regulation of HLA class I expression at the allelic level in freshly isolated leukemic blasts, Cancer Sci., 98(1):102-108 (2007).
McGranahan et al., Allele-specific HLA loss and immune escape in lung cancer evolution, Cell, 171:1259-1271, (2017).
McGranahan, Loss of heterozygosity in human leukocyte antigen, available online at < https://bitbucket.org/mcgranahanlab/lohhla/src/master/ >, 2017, 4 pages.
NCT00393029, Phase II Study of Metastatic Cancer That Overexpresses P53 Using Lymphodepleting Conditioning Followed by Infusion of Anti-P53 TCR-Gene Engineered Lymphocytes, National Cancer Institute (NCI), dirst posted Oct. 26, 2006.
NCT00509288, Phase II Study of Metastatic Melanoma With Lymphodepleting Conditioning and Infusion of Anti-MART-1 F5 TCR-Gene-Engineered Lymphocytes, National Cancer Institute (NCI), first posted Jul. 31, 2007.
NCT00871481, Laboratory-Treated T Cells and Ipilimumab in Treating Patients With Metastatic Melanoma, Fred Hutchinson Cancer Research Center, first posted Mar. 30, 2009.
NCT01069640, Safety Study of Peptide Cancer Vaccine to Treat HLA-A*02-positive Advanced Non-small Cell Lung Cancer, Shiga University, first posted Feb. 17, 2010.
NCT01069653, Safety Study of Peptide Cancer Vaccine to Treat HLA-A*24-positive Advanced Small Cell Lung Cancer, Shiga University, first posted Feb. 17, 2010.
NCT01343043, A Pilot Study of Genetically Engineered NY-ESO-1 Specific NY-ESO-1?²5?T in HLA-A2+ Patients With Synovial Sarcoma (NY-ESO-1), GlaxoSmithKline, first posted Apr. 27, 2011.
NCT01567891, CT Antigen TCR-redirected T Cells for Ovarian Cancer, Adaptimmune, first posted Mar. 30, 2012.
NCT02111850, T Cell Receptor Immunotherapy Targeting MAGE-A3 for Patients With Metastatic Cancer Who Are HLA-DP0401 Positive, National Cancer Institute (NCI), first posted Apr. 11, 2014.

(Continued)

*Primary Examiner* — Jerry Lin
(74) *Attorney, Agent, or Firm* — Marshall, Gerstein & Borun LLP

(57) ABSTRACT

Processes are provided for detecting loss of heterozygosity of Human Leukocyte Antigen (HLA) in a subject using analysis of next generation sequencing (NGS) data. The processes include aligning NGS data and identifying unmapped and mapped reads, updating reference data, and feeding one or more sequence reads to an HLA typing process for identifying candidate HLA alleles and feeding HLA type data to a loss of heterozygosity (LOH) modeling process for determining a LOH status for each HLA allele. A report may be generated of the LOH statuses for each of HLA allele.

30 Claims, 20 Drawing Sheets

(56) References Cited

OTHER PUBLICATIONS

NCT02408016, Genetically Modified T Cells in Treating Patients With Stage III-IV Non-small Cell Lung Cancer or Mesothelioma, Fred Hutchinson Cancer Research Center, first posted Apr. 3, 2015.
NCT02550535, a Phase I/II Study of Gene-modified WT1 TCR Therapy in MDS & AML Patients, Cell Medica Ltd, first posted Sep. 15, 2015.
NCT02570308, A Study of the Intra-Patient Escalation Dosing Regimen With IMCgp100 in Patients With Advanced Uveal Melanoma, Immunocore Ltd, first posted Oct. 7, 2015.
NCT02588612, NY-ESO-1c259T for Advanced NSCLC, GlaxoSmithKline, prist posted Oct. 28, 2015.
NCT02592577, MAGE A10c796T for Advanced NSCLC, Adaptimmune, first posted Oct. 30, 2015.
NCT02636855, Screening Protocol for Tumor Antigen Expression Profiling and HLA Typing for Eligibility Determination, Adaptimmune, first posted Dec. 22, 2015.
NCT02652468, TCR-60 /β and CD19 Depleted Stem Cell Grafts From Haplo Donors for HSCT in Relapsed Lymphoma, University of Wisconsin, Madison, first posted Jan. 11, 2016.
NCT02743611, Safety & Activity of Controllable PRAME-TCR Therapy in Previously Treated AML/MDS or Metastatic Uveal Melanoma, Bellicum Pharmaceuticals, first posted Apr. 19, 2016.
NCT02774291, Anti-ESO (Cancer/Test Antigen) mTCR-transduced Autologous Peripheral Blood Lymphocytes and Combination Chemotherapy in Treating Patients With Metastatic Cancer That Expresses NY-ESO-1, Albert Einstein College of Medicine, first posted May 17, 2016.
NCT02775292, Gene-Modified T Cells, Vaccine Therapy, and Nivolumab in Treating Patients With Stage IV or Locally Advanced Solid Tumors Expressing NY-ESO-1 (NYM), Jonsson Comprehensive Cancer Center, first posted May 17, 2016.
NCT02858310, E7 TCR T Cells for Human Papillomavirus-Associated Cancers, National Cancer Institute (NCI), first posted Aug. 8, 2016.
NCT02869217, Study of TBI-1301 (NY-ESO-1 Specific TCR Gene Transduced Autologous T Lymphocytes) in Patients With Solid Tumors, University Health Network, Toronto, first posted Aug. 16, 2016.
NCT02989064, MAGE-A10c796T for Urothelial Cancer, Melanoma or Head and Neck Cancers, Adaptimmune, first posted Dec. 12, 2016.
NCT02992743, A Pilot Study of NY-ESO-1c259T Cells in Subjects With Advanced Myxoid/ Round Cell Liposarcoma, GlaxoSmithKline, first posted Dec. 14, 2016.
NCT03017131, Genetically Modified T Cells and Decitabine in Treating Patients With Recurrent or Refractory Ovarian, Primary Peritoneal, or Fallopian Tube Cancer, Roswell Park Cancer Institute, first posted Jan. 11, 2017.
NCT03029273, NY-ESO-1 TCR (TAEST16001) for Patients With Advanced NSCLC, Guangzhou Institute of Respiratory Disease, first posted Jan. 24, 2017.
NCT03070392, Safety and Efficacy of IMCgp100 Versus Investigator Choice in Advanced Uveal Melanoma, Immunocore Ltd, first posted Mar. 3, 2017.
NCT03132922, MAGE-A4c1032T for Multi-Tumor, Adaptimmune, first posted Apr. 28, 2017.
NCT03139370, Safety and Efficacy of MAGE-A3/A6 T Cell Receptor Engineered T Cells (KITE-718) in HLA-DPB1*04:01 Positive Adults With Advanced Cancers, Kite, A Gilead Company, first posted May 3, 2017.
NCT03159585, to Evaluate the Efficacy of NY-ESO-1-specific T Cell Receptor Affinity Enhancing Specific T Cell in Solid Tumors, Zhujiang Hospital, first posted May 18, 2017.
NCT03168438, NY-ES0-1c259T Alone and in Combination With Pembrolizumab for Multiple Myeloma, GlaxoSmithKline, first posted May 30, 2017.
NCT03190941, Administering Peripheral Blood Lymphocytes Transduced With a Murine T-Cell Receptor Recognizing the G12V Variant of Mutated RAS IN HLA-A*11:01 Patients, National Cancer Institute (NCI), first posted Jun. 19, 2017.
NCT03240861, Genetically Engineered PBMC and PBSC Expressing NY-ESO-1 TCR After a Myeloablative Conditioning Regimen to Treat Patients With Advanced Cancer (NYESO SCT), Jonsson Comprehensive Cancer Center, first posted Aug. 7, 2017.
NCT03247309, TCR-engineered T Cells in Solid Tumors With Emphasis on NSCLC and HNSCC (ACTengine), Immatics US, Inc., first posted Aug. 11, 2017.
NCT03318900, T-Cell Infusion, Aldesleukin, and Utomilumab in Treating Patients With Recurrent Ovarian Cancer, M.D. Anderson Cancer Center, first posted Oct. 24, 2017.
NCT03326921, HA-1 T TCR T Cell Immunotherapy for the Treating of Patients With Relapsed or Refractory Acute Leukemia After Donor Stem Cell Transplant, Fred Hutchinson Cancer Research Center, first posted Oct. 31, 2017.
NCT03399448, NY-ESO-1-redirected CRISPR (TCRendo and PD1) Edited T Cells (NYCE T Cells), University of Pennsylvania, first posted Jan. 16, 2018.
NCT03441100, TCR-engineered T Cells in Solid Tumors Including NSCLC and HCC Patients (ACTengine), Immatics US, Inc., first posted Feb. 22, 2018.
NCT03503968, TCR Modified T Cells MDG1011 in High Risk Myeloid and Lymphoid Neoplasms, Medigene AG, first posted Apr. 20, 2018.
NCT03515551, Safety and Efficacy of IMCnyeso in Advanced NY-ESO-1 and/or LAGE-1A Positive Cancers, Immunocore Ltd, first posted May 3, 2018.
NCT03649529, Treatment of Malignant Melanoma With GPA-TriMAR-T Cell Therapy, Timmune Biotech Inc., first posted Aug. 28, 2018.
NCT03686124, TCR-engineered T Cells in Solid Tumors, Immatics US, Inc., first posted Sep. 26, 2018.
NCT03691376, Genetically Engineered Cells (NY-ESO-1 TCR Engineered T Cells and HSCs) After Melphalan Conditioning Regimen in Treating Patients With Recurrent or Refractory Ovarian, Fallopian Tube, or Primary Peritoneal Cancer, Roswell Park Cancer Institute, first posted Oct. 1, 2018.
NCT03709706, Pilot Immunotherapy Study With Autologous T-cells Specific for New York Esophageal Antigen-1 (NY-ESO-1)/ Cancer-testis Antigen-2 (LAGE-1a)-Positive Advanced Non-small Cell Lung Cancer (NSCLC) Either Alone or in Combination With Pembrolizumab, GlaxoSmithKline, first posted Oct. 17, 2018.
NCT03745326, Administering Peripheral Blood Lymphocytes Transduced With a Murine T-Cell Receptor Recognizing the G12D Variant of Mutated RAS in HLA-A*11:01 Patients, National Cancer Institute (NCI), first posted Nov. 19, 2018.
NCT03747484, Gene-Modified Immune Cells (FH-MCVA2TCR) in Treating Patients With Metastatic or Unresectable Merkel Cell Cancer, Fred Hutchinson Cancer Research Center, first posted Nov. 20, 2018.
NCT03912831, Safety and Efficacy of KITE-439 in HLA-A*02:01+ Adults With Relapsed/Refractory HPV16+ Cancers, Kite, A Gilead Company, first posted Apr. 11, 2019.
NCT03925896, Phase I Trial of LMP2 Antigen-specific TCR T-cell Therapy for Recurrent and Metastatic NPC Patients, Sun Yat-sen University, first posted Apr. 24, 2019.
NCT03970382, A Study of Gene Edited Autologous Neoantigen Targeted TCR T Cells With or Without Anti-PD-1 in Patients With Solid Tumors, PACT Pharma, Inc., first posted May 31, 2019.
NCT03973333, Safety and Efficacy of IMC-C103C as Monotherapy and in Combination With Atezolizumab, Immunocore Ltd, first posted Jun. 4, 2019.
Newburn, Understanding the role of Human Leukocyte Antigen in Cancer Immunotherapy, Personalis, available online at < https://www.personalis.com/understanding-role-human-leukocyte-antigen-cancer-immunotherapy/ >, 2020, 4 pages.
Rosenthal et al., HLA LOH As an Immune Evasive Mechanism in TRACERx NSCLC, 2018, available online at < https://www.lungcancernews.org/2018/06/04/hla-loh-as-an-immune-evasive-mechanism-in-tracerx-nscic/ >, 5 pages.
Rosenthal et al., Neoantigen-directed immune escape in lung cancer evolution, Nature, 567:479-485 (2019).

(56) References Cited

OTHER PUBLICATIONS

Scheper et al., Low and variable tumor reactivity of the intratumoral TCR repertoire in human cancers, Nat. Med., 25:89-94 (2019).
Seidel et al., Anti-PD-1 and Anti-CTLA-4 therapies in cancer: Mechanisms of action, Efficacy, and limitations, Front. Oncol., 8:86 (2018).
Staff reporter, BRCA1/2 LOH Testing May Offer Treatment Response Clues in Some Cancer Cases, Genome Web, 2017.
Szolek et al., OptiType: precision HLA typing from next-generation sequencing data, Bioinformatics, 30:3310-3316 (2014).
Tran et al., T-Cell transfer therapy targeting mutant KRAS in cancer, N. Engl. J. Med. 375:2255-2262 (2016).
Chen et al., Single nucleotide polymorphisms within HLA region are associated with disease relapse for patients with unrelated cord blood transplantation., PeerJ., 6:e5228 (2018).
Clark et al., U87MG Decoded: The Genomic Sequence of a Cytogenetically Aberrant Human Cancer Cell Line., PLoS Genet, 6(1):e1000632 (2010).
International Application No. PCT/US2020/018014, International Search Report and Written Opinion, dated Jul. 31, 2020.
International Application No. PCT/US2020/018014, Invitation to Pay Additional Fees, dated May 11, 2020.
Tschochner et al., Identifying Patient-Specific Epstein-Barr Nuclear Antigen-1 Genetic Variation and Potential Autoreactive Targets Relevant to Multiple Sclerosis Pathogenesis, Plos One., 11(2):e0147567 (2016).

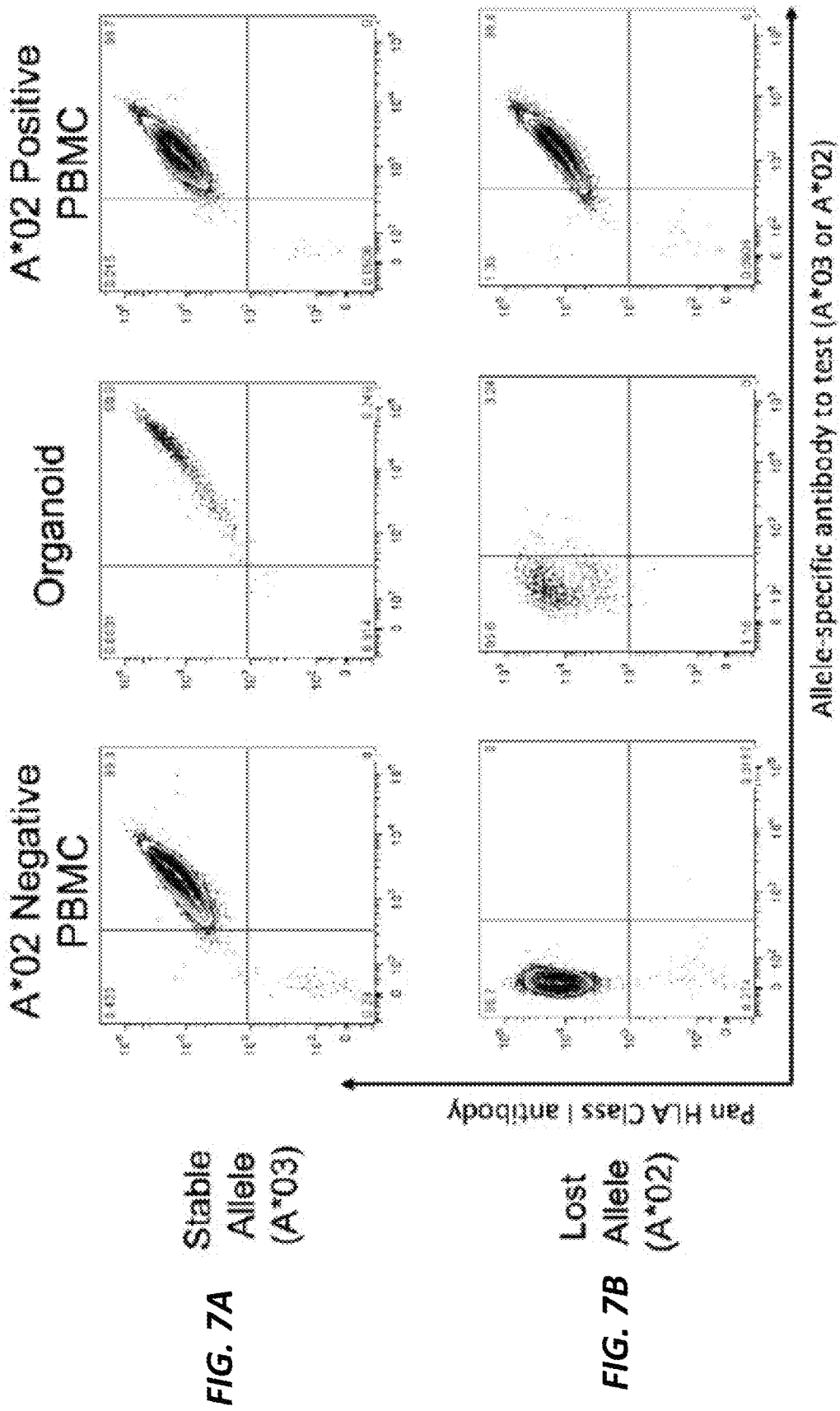

| Cancer Cohort | Percent with LOH | Number of Sample |
|---|---|---|
| Colorectal | 30% | 50 |
| Lung | 26% | 50 |
| Ovarian | 20% | 50 |
| Breast | 16% | 50 |
| Pancreatic | 10% | 50 |
| Brain | 8% | 50 |
| Endometrial | 8% | 50 |

*FIG. 13*

DETECTION OF HUMAN LEUKOCYTE ANTIGEN LOSS OF HETEROZYGOSITY

CROSS-REFERENCE TO RELATED APPLICATIONS

This application claims priority to U.S. Provisional Patent Application No. 62/804,501, filed Feb. 12, 2019, U.S. Provisional Patent Application No. 62/889,510, filed Aug. 20, 2019 and U.S. Provisional Patent Application No. 62/932,090, filed Nov. 7, 2019, all of which are hereby incorporated by reference in their entirety.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Human Leukocyte Antigen Class I (HLA) proteins are expressed on the surface of all nucleated cells and are vital for immune surveillance. When tumor-specific mutations (neoantigens) are presented on HLA molecules to CD8+ T cells, this recognition can drive immune responses against the tumor and lead to tumor destruction. One mechanism of immune escape for tumors is loss of heterozygosity in HLA genes (HLA-LOH), which reduces the total number of neoantigens that can be presented to T cells. Due to the highly polymorphic nature of HLA, the copy number status of HLA genes is extremely challenging to assess by standard bioinformatics approaches.

SUMMARY

In accordance with an example, a computer-implemented method for detecting loss of heterozygosity of Human Leukocyte Antigen (HLA) in a subject, the method comprises: receiving next generation sequencing data collected from an isolated tissue biological sample from the subject; aligning the next generation sequencing data against a reference genome and determining genetic positions indicating locations in the reference genome of mapped reads having a sequence that map to the reference genome and determining unmapped reads in the next generation sequencing data, and storing mapped reads data and unmapped reads data into one or more sequence reads files, first data file and a reverse reads, second data files; feeding the one or more sequence reads files to an HLA typing process and identifying candidate HLA alleles and storing the candidate HLA alleles as HLA type data in an HLA reference file; feeding the HLA type data in the HLA reference file and optionally feeding the one or more sequence reads files to a loss of heterozygosity (LOH) modeling process and determining, using the LOH modeling process, a LOH status for each HLA allele; and generating and storing a report of the LOH statuses for each of the HLA alleles.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 5A shows data that were calculated using all disclosed steps and features, FIG. 5B shows data calculated without aligning discarded/unmapped reads to HLA genes, and FIG. 5C shows data calculated without replacing the HLA reference sequences with the variants detected in the sequence data generated by the patient sample. Light colors (lighter blue and lighter red) indicate areas of low coverage and black dots indicate positions where the sequences of the two alleles diverge from one another.

FIGS. 7A and 7B collectively illustrate the results of an optional biological assay used to validate the predictions of the HLA and LOH model.

FIG. 8A shows coverage data calculated for the non-cancer sample. FIG. 8B shows coverage data calculated for the cancer sample tissue extracted from the same patient as the non-cancer sample. FIG. 8C shows coverage data for a tumor organoid derived from the cancer sample tissue.

FIG. 13 is a table showing the percent and number of samples in the xT 500 cohort predicted to have HLA-LOH by the model, categorized by cancer type.

DETAILED DESCRIPTION

Definitions

Figure 1:
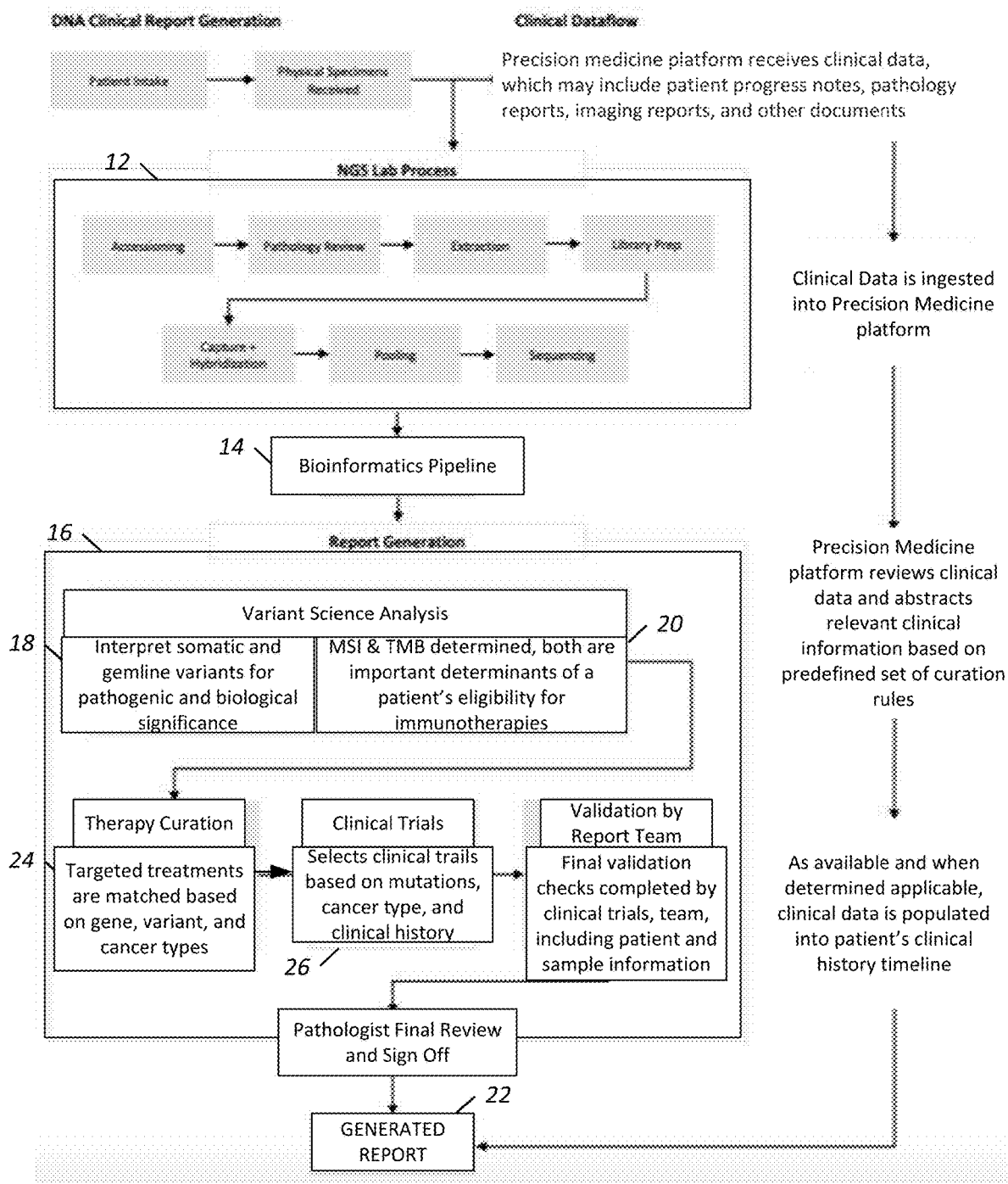
FIG. 1 illustrates an example workflow 10 for next generation sequencing, bioinformatics processing, and report generation, in an example.

"Pseudogene" means a non-functional HLA gene (for example, HLA-Y) and/or an HLA gene that isn't expressed. HLA pseudogenes may not impact a patient's health, immune system activity and/or control of cancer cells, but these pseudogenes may have genetic sequences that are similar to the genetic sequences of functional HLA genes, such that sequence reads from HLA pseudogenes could potentially align to functional HLA genes.

"Genetic analyzer" means a device, system, and/or methods for determining the characteristics (including sequences) of nucleic acid molecules (including DNA, RNA, etc.) present in biological specimens (including tumors, biopsies, tumor organoids, blood samples, saliva samples, or other tissues or fluids).

"Targeted Panel" means a combination of probes for next-generation sequencing of a patient's biological specimens (including tumors, biopsies, tumor organoids, blood samples, saliva samples, or other tissues or fluids) which are selected to map one or more loci on one or more chromosomes.

"Sequencing probe" means a collection of chemicals which attach to a locus of a chromosome based on the expected sequence of nucleotides at the RNA or DNA present at that locus.

"RNA read count" means the read counts of RNA or cDNA generated from a genetic analyzer.

"Bioinformatics pipeline" means a series of processing stages of a pipeline to instantiate bioinformatics reporting regarding next-generation sequencing results of a patient's tumor or normal tissue or bodily fluids to extract and report on variants present in the patient's genome.

"Genetic profile" means a combination of one or more variants, RNA transcriptomes, or other informative genetic characteristics determined for a patient from next-generation sequencing.

"Genetic sequence" means a recordation of a series of nucleotides present in a patient's RNA or DNA as determined from sequencing the patient's tissue or fluids.

"Variant" means a difference in a genetic sequence or genetic profile when compared to a reference genetic sequence or expected genetic profile.

"Expression level" means the number of copies of an RNA or protein molecule generated by a gene or other genetic locus, which may be defined by a chromosomal location or other genetic mapping indicator.

"Gene product" means a molecule (including a protein or RNA molecule) generated by the manipulation (including transcription) of the gene or other genetic locus, which may be defined by a chromosomal location or other genetic mapping indicator.

DNA Next-Generation Sequencing (NGS) revolutionized genomic research; yet, an inherent limitation to NGS is the requirement for a reference genome for data analysis. The reference genome serves as a template against which "reads" (i.e., short oligonucleotide sequences corresponding to portions of a target DNA or RNA, although NGS may also include long-read NGS and nanopore sequencing techniques) are aligned to elucidate the full length sequence of a target DNA or RNA. The requirement for a reference genome severely complicates use of the technology to characterize highly variable biomarkers, such as HLA, as the diversity of sequences is not reflected in reference genomes. More than 22,000 alleles have been identified in worldwide populations at 12 expressed Class I and II loci. (Williams, J Mol Diagn. 2001 August; 3(3): 98-104, citing European Bioinformatics Institute, ebi.ac.uk/imgt/hla) Class I genes include HLA-A, -B, and -C, as well as the non-classical MHC-Ib genes HLA-E, -F, and -G. Class II genes include DRA, DRB1, DQA1, DQB1, DPA1, and DPB1. Multiple alleles exist for each genetic locus.

The polymorphic nature of HLA is an important evolutionary development, as it allows the population to display a wide range of antigens to the immune system. The large degree of polymorphism at the Class I and Class II loci, however, poses a significant challenge for detecting mutation and loss of heterozygosity.

The instant disclosure provides methods and systems for overcoming the limitations associated with NGS to efficiently and accurately detect loss of heterozygosity (LOH) of HLA (also termed "HLA-LOH" herein) in a subject, especially in cancer cells within a subject. HLA-LOH may occur in cancer cells without occurring in the healthy/non-cancer cells in a subject.

The HLA-LOH processes herein may be executed on one or more network accessible computer processing systems, including network accessible devices communicatively coupled to other computer systems, such as other NGS systems. In some examples, the processes include, initially receiving genetic material (DNA or RNA) isolated from a patient specimen and sequenced, for example, using a NGS technique. In other examples, the processes may receive only the sequence data. The specimen may be any biological sample obtained from the patient, such as a tissue sample (e.g., tumor tissue from a biopsy), a cell sample, blood, saliva, urine, and the like. Both cancer and non-cancer specimens may be isolated and sequenced by the computer processing systems performing the HLA-LOH processes, and such systems may store the sequence data in a set of data files for the cancer specimens and a set of data files for non-cancer specimens. Each file may be configured to store the sequence of each detected read and the number of times (counts) that a sequence was detected. Example data file formats include a BCL file or a FASTQ file, where the FASTQ format further includes a quality score for each read.

In some examples, the computer processing systems may pre-process the sequence data by filtering and/or cleaning the data and align that pre-processed data against a reference genome, for example, using a bioinformatics pipeline executed using the computer processing system. In some examples, the reference genome build is the hg19 genome (see, e.g., GenBank assembly accession: GCA_000001405.1). In the genetic sequence of HLA genes there can be considerable variety from person to person, however the hg19 genome contains only one allele for each HLA gene; therefore many reads detected from the HLA genes may not map to hg19. In some examples, the normalization and alignment for sequence data occurs for both cancer and non-cancer specimens, yielding a set of output files for cancer specimens and a set of output files for non-cancer specimens. The output files may store genetic positions indicating the location in the reference genome that matches the sequence of each read, and additional information relating to mapping attributes and mapping quality of each read. Example file formats include a BAM file. For example, the process generates normal tissue BAM files and tumor tissue BAM files. Unmapped reads, that is, reads that do not match the genome with quality scores that exceed quality thresholds, are stored in the BAM file with corresponding read flags indicating that the read did not map successfully. This may be due to high numbers of mismatched bases or a high degree of multimapping. In some examples, reads bearing this unmapped flag are generally excluded from downstream analysis (variant calling, etc.).

FIG. 1 illustrates an example workflow 10 for next generation sequencing, bioinformatics processing, and report generation, in an example. In various embodiments, cancer samples and non-cancer samples may be processed by DNA next generation sequencing (NGS) 12, designed to sequence either the whole exome or a targeted panel of cancer-related genes, to generate DNA sequencing data, and the DNA sequencing data may be processed by a bioinformatics pipeline 14 to generate HLA-LOH results (among other outputs) for each sample. The cancer sample may be a tissue sample or blood sample containing cancer cells. In some instances, a tumor organoid sample may be processed instead of the patient cancer sample.

In more detail, germline ("normal", non-cancerous) DNA may be extracted from either blood (for example, if a patient has cancer that is not a blood cancer) or saliva (for example, if a patient has blood cancer). Normal blood samples may be collected from patients (for example, in PAXgene Blood DNA Tubes) and saliva samples may be collected from patients (for example, in Oragene DNA Saliva Kits).

Blood cancer samples may be collected from patients (for example, in EDTA collection tubes). Macrodissected FFPE tissue sections (which may be mounted on a histopathology slide) from solid tumor samples may be analyzed by pathologists to determine overall tumor amount in the sample and percent tumor cellularity as a ratio of tumor to normal nuclei. For each section, background tissue may be excluded or removed such that the section meets a tumor purity threshold (in one example, at least 20% of the nuclei in the section are tumor nuclei).

Then, DNA may be isolated from blood samples, saliva samples, and tissue sections using commercially available reagents, including proteinase K to generate a liquid solution of DNA.

Each solution of isolated DNA may be subjected to a quality control protocol to determine the concentration and/or quantity of the DNA molecules in the solution, which may include the use of a fluorescent dye and a fluorescence microplate reader, standard spectrofluorometer, or filter fluorometer.

For each cancer sample and each normal sample, isolated DNA molecules may be mechanically sheared to an average length using an ultrasonicator (for example, a Covaris ultrasonicator). The DNA molecules may also be analyzed to determine their fragment size, which may be done through gel electrophoresis techniques and may include the use of a device such as a LabChip GX Touch.

DNA libraries may be prepared from the isolated DNA, for example, using the KAPA Hyper Prep Kit, a New England Biolabs (NEB) kit, or a similar kit. DNA library preparation may include the ligation of adapters onto the DNA molecules. For example, UDI adapters, including Roche SeqCap dual end adapters, or UMI adapters (for example, full length or stubby Y adapters) may be ligated to the DNA molecules.

In this example, adapters are nucleic acid molecules that may serve as barcodes to identify DNA molecules according to the sample from which they were derived and/or to facilitate the downstream bioinformatics processing and/or the next generation sequencing reaction. The sequence of nucleotides in the adapters may be specific to a sample in order to distinguish samples. The adapters may facilitate the binding of the DNA molecules to anchor oligonucleotide molecules on the sequencer flow cell and may serve as a seed for the sequencing process by providing a starting point for the sequencing reaction.

DNA libraries may be amplified and purified using reagents, for example, Axygen MAG PCR clean up beads. Then the concentration and/or quantity of the DNA molecules may be quantified using a fluorescent dye and a fluorescence microplate reader, standard spectrofluorometer, or filter fluorometer.

DNA libraries may be pooled (two or more DNA libraries may be mixed to create a pool) and treated with reagents to reduce off-target capture, for example Human COT-1 and/or IDT xGen Universal Blockers. Pools may be dried in a vacufuge and resuspended. DNA libraries or pools may be hybridized to a probe set (for example, a probe set specific to a panel that includes approximately 100, 600, 1,000, 10,000, etc. of the 19,000 known human genes, IDT xGen Exome Research Panel v1.0 probes, IDT xGen Exome Research Panel v2.0 probes, other IDT probe panels, Roche probe panels, another probe panel that captures the human exome, or another probe panel), and amplified with commercially available reagents (for example, the KAPA HiFi HotStart ReadyMix).

Pools may be incubated in an incubator, PCR machine, water bath, or other temperature modulating device to allow probes to hybridize. Pools may then be mixed with Streptavidin-coated beads or another means for capturing hybridized DNA-probe molecules, especially DNA molecules representing exons of the human genome and/or genes selected for a genetic panel.

Pools may be amplified and purified more than once using commercially available reagents, for example, the KAPA HiFi Library Amplification kit and Axygen MAG PCR clean up beads, respectively. The pools or DNA libraries may be analyzed to determine the concentration or quantity of DNA molecules, for example by using a fluorescent dye (for example, PicoGreen pool quantification) and a fluorescence microplate reader, standard spectrofluorometer, or filter fluorometer.

In one example, the DNA library preparation and/or whole exome capture steps of the process 12 may be performed partially or wholly with an automated system, using a liquid handling robot (for example, a SciClone NGSx).

The library amplification may be performed on a device, for example, an Illumina C-Bot2, and the resulting flow cell containing amplified target-captured DNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. Samples may be further assessed for uniformity with each sample required to have 95% of all targeted bp sequenced to a minimum depth selected by the user, for example, 300×. The next generation sequencer may generate a FASTQ, BCL, or other file for each flow cell or each patient sample.

In various embodiments, the bioinformatics pipeline 14 may filter FASTQ data obtained from the NGS Lab process 12. Filtering FASTQ data may include correcting sequencer errors and removing (trimming) low quality sequences or bases, adapter sequences, contaminations, chimeric reads, overrepresented sequences, biases caused by library preparation, amplification, or capture, and other errors. Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools, for example Skewer (see doi.org/10.1186/1471-2105-15-182). FASTQ files may be analyzed for rapid assessment of quality control and reads, for example, by a sequencing data QC software such as AfterQC, Kraken, RNA-SeQC, FastQC, (see Illumina, BaseSpace Labs or illumina.com/products/by-type/informatics-products/basespace-sequence-hub/apps/fastqc.html), or another similar software program. For paired-end reads, reads may be merged.

As executed by the bioinformatics pipeline 14, for each FASTQ file, each read in the file may be aligned to the location in the human genome having a sequence that best matches the sequence of nucleotides in the read. There are many software programs designed to align reads, for example, Novoalign (Novocraft, Inc.), Bowtie, Burrows Wheeler Aligner (BWA), programs that use a Smith-Waterman algorithm, etc. Alignment may be directed using a reference genome (for example, hg19, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may generate a SAM file, which stores the locations of the start and end of each read according to coordinates in the reference genome and the coverage (number of reads) for each nucleotide in the reference genome. The SAM files may be converted to BAM files, BAM files may be sorted, and duplicate reads may be marked for deletion, resulting in de-duplicated BAM files.

A BAM file may contain reads from both a cancer sample and a normal sample, and these samples may be derived from the same patient.

The systems and methods described herein may be used to determine whether a patient sample has HLA-LOH, for example.

In various embodiments, BAM files may be analyzed to detect genetic variants, including single nucleotide variants (SNVs), copy number variants (CNVs), gene rearrangements, etc. For example, following alignment and sorting, SNVs may be called by creating a list of locations in the reads associated with a sample where the nucleotide base is not the same as the nucleotide base in that position in the reference genome, and storing that list in a variant call format (VCF) file for the sample.

To assess copy number, de-duplicated BAM files and a VCF generated from the variant calling pipeline may be used to compute read depth and variation in heterozygous germline SNVs between the tumor and normal samples (or between the tumor sample and a pool of process matched normal controls for tumor-only cases when the matched normal sample is not available). Circular binary segmentation may be applied and segments may be selected with highly differential log 2 ratios between the tumor and its comparator (matched normal or normal pool). Approximate integer copy number may be assessed from a combination of differential coverage in segmented regions and an estimate of stromal admixture (for example, tumor purity, or the portion of a sample that is tumor vs. non-tumor) generated by analysis of heterozygous germline SNVs. In various embodiments, the copy number status of chromosome (chr) 6 and/or arms or other portions of chr 6 in the tumor sample and/or the normal sample may be detected by the bioinformatics pipeline and/or received by the systems and methods.

To detect gene rearrangements, following de-multiplexing, tumor FASTQ files may be aligned against the human reference genome using BWA for DNA files. DNA reads may be sorted and duplicates may be marked with a software, for example, SAMBlaster. Discordant and split reads may be further identified and separated. These data may be read into a software, for example, LUMPY, for structural variant detection. Structural alterations may be grouped by type, recurrence, and presence and stored within a database and displayed through a fusion viewer software tool. The fusion viewer software tool may reference a database, for example, Ensembl, to determine the gene and proximal exons surrounding the breakpoint for any possible transcript generated across the breakpoint. The fusion viewer tool may then place the breakpoint 5' or 3' to the subsequent exon in the direction of transcription. For inversions, this orientation may be reversed for the inverted gene. After positioning of the breakpoint, the translated amino acid sequences may be generated for both genes in the chimeric protein, and a plot may be generated containing the remaining functional domains for each protein, as returned from a database, for example, Uniprot.

A report generation process 16 may be used for variant classification and reporting. The process 16 may detect variants and investigate detected variants following criteria from known evolutionary models, functional data, clinical data, literature, and other research endeavors, including tumor organoid experiments. At a process 18, variants may be prioritized and classified based on known gene-disease relationships, hotspot regions within genes, internal and external somatic databases, primary literature, and other features of somatic drivers. Variants may be added to a patient (or sample, for example, organoid sample) report based on recommendations from the AMP/ASCO/CAP guidelines. Additional guidelines may be followed. Briefly, pathogenic variants with therapeutic, diagnostic, or prognostic significance may be prioritized in the report. Non-actionable pathogenic variants may be included as biologically relevant, followed by variants of uncertain significance. Translocations may be reported based on features of known gene fusions, relevant breakpoints, and biological relevance. Evidence may be curated from public and private databases or research and presented as 1) consensus guidelines 2) clinical research, or 3) case studies, with a link to the supporting literature. Germline alterations may be reported as secondary findings in a subset of genes for consenting patients. These may include genes recommended by the ACMG and additional genes associated with cancer predisposition or drug resistance.

For detecting microsatellite instability status (MSI), the probes used during library preparation before sequencing may target microsatellite regions (for example, approximately 40, 50, 60, 100, 1,000 regions). At a process 20, a MSI classification algorithm classifies tumors into three categories: microsatellite instability-high (MSI-H), microsatellite stable (MSS), or microsatellite equivocal (MSE). MSI testing for paired tumor-normal patients may use reads mapped to the microsatellite loci with at least five, ten, fifteen, etc. bp flanking the microsatellite region. A minimum read threshold may be used. For example, the identification of at least 10, 20, 30, etc. mapping reads in both tumor and normal samples may be required for the locus to be included in the analysis. A minimum coverage threshold may be used. For example, At least 10, 15, 20, etc. of the total microsatellites on the panel may be required to reach the minimum coverage. Each locus may be individually tested for instability, as measured by changes in the number of nucleotide base repeats in tumor data compared to normal data, for example, using the Kolmogorov-Smirnov test. If $p \leq 0.05$, the locus may be considered unstable. The proportion of unstable microsatellite loci may be fed into a logistic regression classifier trained on samples from various cancer types, especially cancer types which have clinically determined MSI statuses, for example, colorectal and endometrial cohorts. For MSI testing in tumor-only mode, the mean and variance for the number of repeats may be calculated for each microsatellite locus. A vector containing the mean and variance data may be put into a support vector machine classification algorithm. Both algorithms may return the probability of the patient being MSI-H as an output which may be compared to a threshold value.

In one example, if there is a >70% probability of MSI-H status, the sample may be classified as MSI-H. If there is between a 30-70% probability of MSI-H status, the test results may be too ambiguous to interpret and those samples may be classified as MSE. If there is a <30% probability of MSI-HMSI-H status, the sample may be considered MSS.

A patient report may be generated at a process 16. The report may be presented to a patient, physician, medical personnel, or researcher in a digital copy (for example, a JSON object, pdf file, or an image on a website or portal), a hard copy (for example, printed on paper or another tangible medium), as audio (for example, recorded or streaming audio), or in another format.

The report may include information related to the lost or present HLA alleles, including clinical trials for which the patient is eligible, therapies that may match the patient (for example, the systems and methods may be used as a companion diagnostic for these therapies) and/or adverse effects predicted if the patient receives a given therapy, based on the present or lost HLA alleles in the patient's tumor (obtained using a process 24). For example, the report may include information related to whether the patient's tumor is potentially-resistant to HLA-restricted immunotherapies (for example, cellular TCR therapies, vaccines, and immunotherapies designed to be most efficacious in the presence of a particular HLA allele or alleles, etc). Alternatively, the report may include information related to whether the patient's tumor is potentially a good candidate for HLA-restricted immunotherapies (for example, cellular TCR therapies, vaccines, and immunotherapies designed to be most efficacious in the absence of a particular HLA allele or alleles, etc.). The report may state that the patient may not respond to immunotherapies that target HLA alleles that have been lost in the patient sample, may or may not be eligible for clinical trials listing the loss or presence of those HLA alleles as inclusion or exclusion criteria (obtained using a process 26). On the contrary, treatments (for example, immunotherapies) based on any HLA alleles present in the patient sample may be matched to the patient (for example, the systems and methods may be used as a companion diagnostic for these treatments) and the patient may be eligible for clinical trials listing present HLA alleles as inclusion criteria, and may not be eligible for clinical trials listing present HLA alleles as exclusion criteria (as obtained using process 26). The report may further include the copy number status of chr 6 and/or arms or portions of chr 6 in the tumor sample and/or normal sample. In various embodiments, if the copy number of at least a portion of chr 6 (particularly the short arm of chr6, for example 6p, including the regions surrounding the HLA locus (for example, the Class I and/or Class II locus) is less than two in the tumor sample (for example, implying that there is a loss of a copy of at least a portion of a copy of chr 6) the report may infer HLA-LOH for that sample.

In one example, information related to a loss of a portion of chr 6 does not specify which copy of an HLA allele was contained on the lost copy of a portion of chr 6 but provides supporting evidence that one of the HLA alleles was lost. For example, the allele specific systems and methods described herein conclude that coverage of Allele B is lower than coverage of Allele A, but the coverage of Allele B is close to the threshold for calling LOH, resulting in an equivocal LOH call, which may be caused by standard variability in coverage or may reflect a partial loss or actual loss of the HLA allele. In that case, the chr6 LOH status serves as an orthogonal way to confirm that loss or presence of the HLA allele. For example, if a copy of the portion of chr6 containing the HLA allele is lost, then the HLA allele that was called as equivocal loss status by the systems and methods described herein may be called as LOH. On the contrary, if no portions of chr6 are reported lost, the HLA allele with an equivocal LOH call may be determined to be present.

In various embodiments, the HLA-LOH results may be used to analyze a database of clinical data, especially to determine whether there is a trend showing that a therapy slowed cancer progression in other patients having the same or similar lost/present status as the results for a given HLA allele. The LOH results may also be used to design tumor organoid experiments. For example, an organoid may be genetically engineered to have the same HLA alleles present as a patient and may be observed after exposure to a therapy to determine whether the therapy can reduce the growth rate of the organoid, and thus may be likely to reduce the progression of cancer in the patient associated with the specimen.

Figure 2:
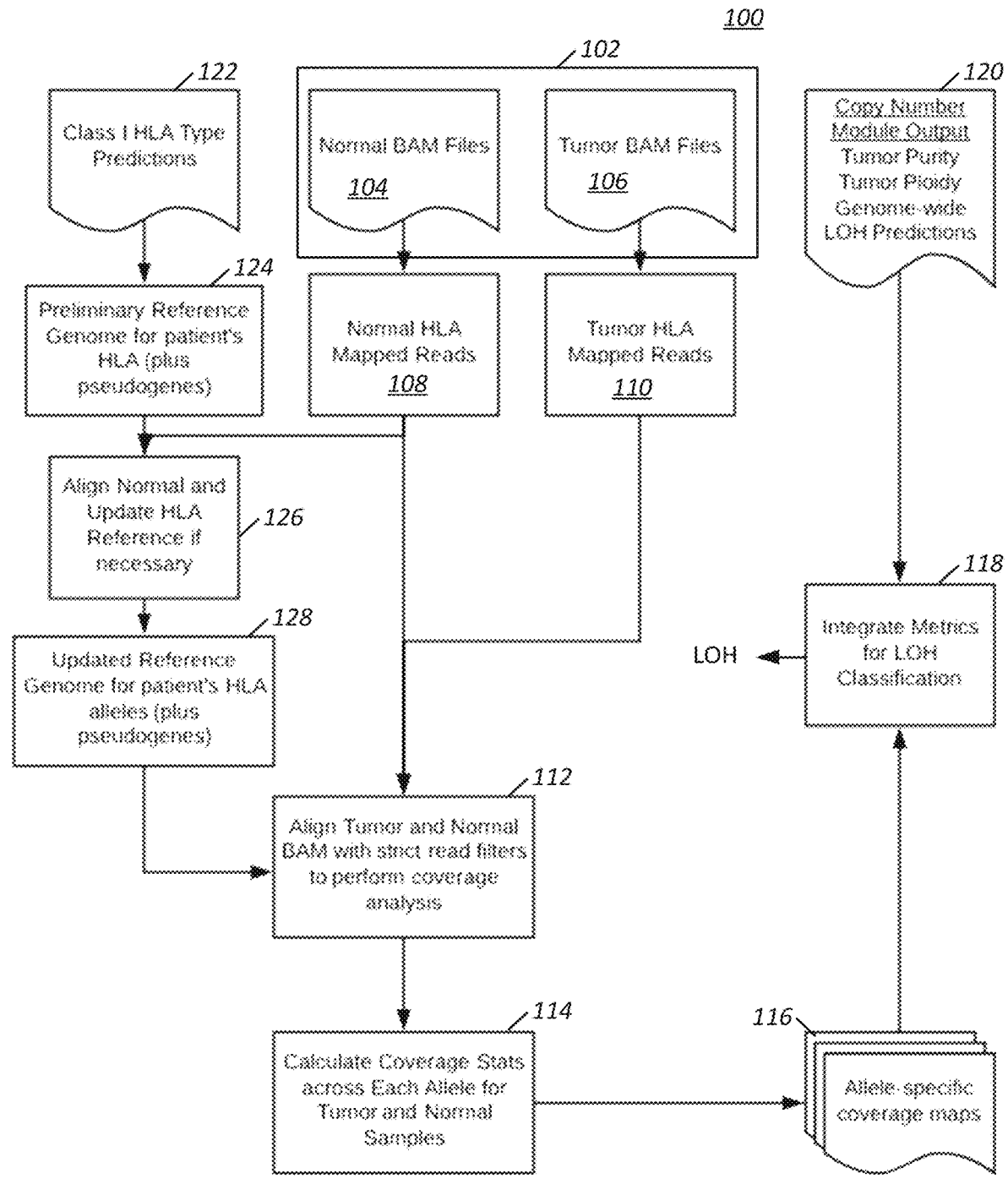
FIG. 2 illustrates an overall schematic of an example process for Human Leukocyte Antigen Class I (HLA) detection and analysis.
Figure 10:
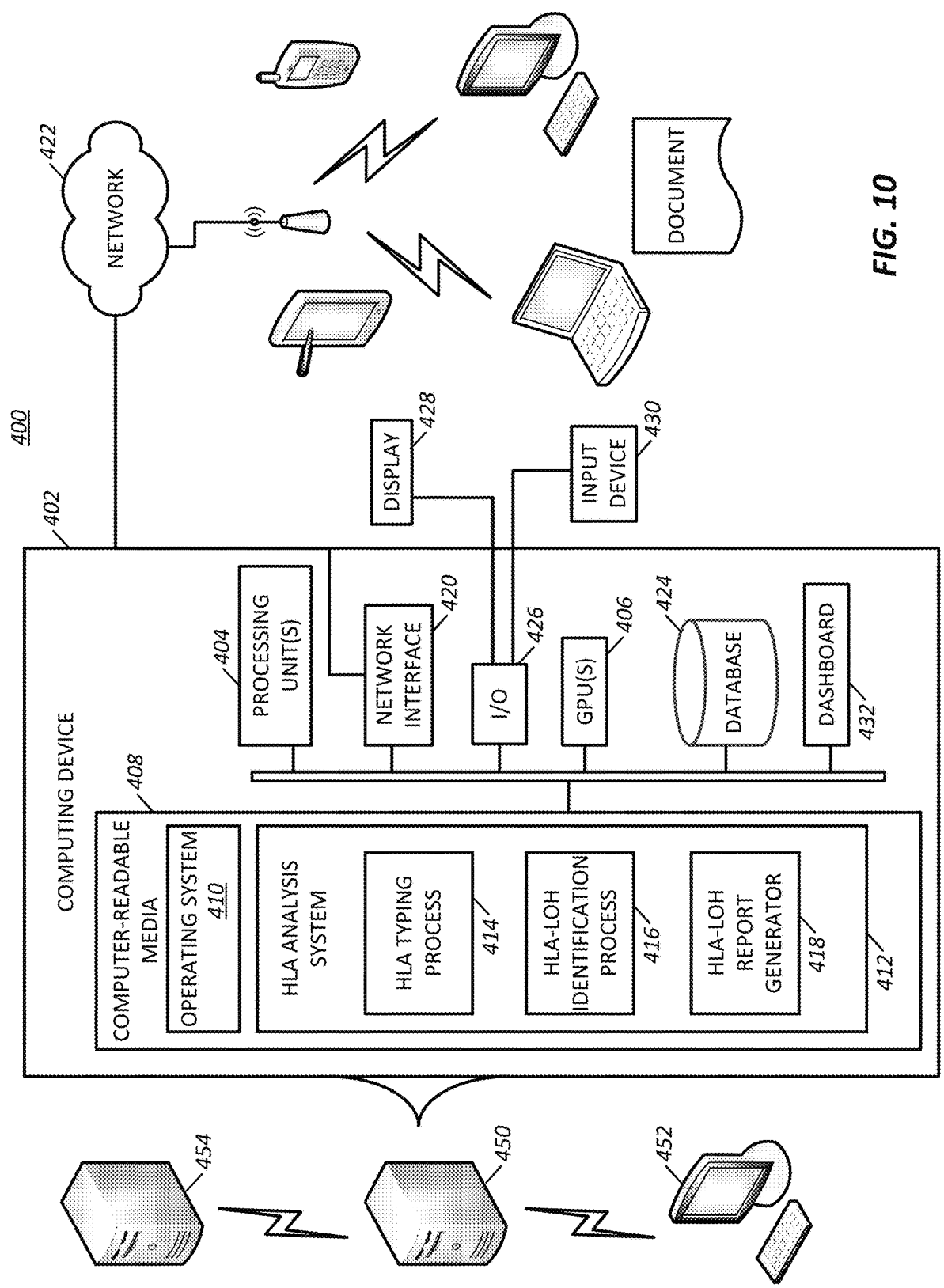
FIG. 10 illustrates an example system for HLA and HLA-LOH analysis that may be implemented on a network accessible processing system for performing the processes described herein.

FIG. 2 illustrates an overall schematic of an example process 100 for HLA detection and analysis that may be performed by an HLA and HLA-LOH analysis system, such as that shown in FIG. 10. In the example illustrated, the HLA and HLA-LOH analysis system access stored genomic sequence data collected from normal tissue and from cancer tissue. More specifically, in the illustrated example, the process 100 accesses BAM files 102 containing non-cancer specimens with sequence data stored in a normal BAM file 104 and/or cancer specimens with sequence data stored in a tumor BAM file 106. At a next step, the process 100 retrieves normal tissue (or blood) HLA mapping reads 108 from the normal BAM file 104 and tumor tissue HLA mapping reads 110 from the tumor BAM file 106.

In the illustrated example, the normal tissue HLA mapping reads and the tumor tissue HLA mapping reads, from files 108 and 110, respectively, are communicated to or accessed by an alignment process 112. As discussed further herein, the alignment process 112 aligns tumor tissue data from the BAM file 106, i.e., the tumor HLA mapped reads 110, with normal tissue data from the BAM file 104, i.e., the normal HLA mapped reads 108. In various examples, the alignment process 112 applies one or more read filters to the BAM file data prior to alignment. These filters may be applied to each HLA mapped reads data, normal tissue and tumor tissue. The filters may be applied to only one of the HLA mapped reads, normal tissue or tumor tissue. The filters may be stored in a hierarchical manner by the HLA and HLA-LOH analysis system, where the system applies a filters in order based on ranking, with higher ranking filters applied before lower ranked filters, and, in some examples, with an assessment of filter performance, whereby if a higher ranked filter achieves a desired filtering result, lower ranked filters are not executed by the system.

The output from the alignment process 112 is provided to a coverage statistics process 114, that compares the aligned HLA mapped reads for normal tumor tissue and calculates coverage metrics for each allele for the normal tissue and tumor tissue data. The process 114 generates a report in the form of HLA allele-based coverage data 116, where that report may be stored in the system, displayed to medical personnel, and/or sent to a networked connected device, database, etc. In this way, the processes 112, 114, and 116 form an example HLA typing process.

To generate HLA-LOH data, the HLA allele-based coverage data 116 is provided to an HLA-LOH process 118, which in the illustrated example is configured to receive other data, such as tumor purity data, tumor ploidy data, and/or genome-wide LOH predictions (collectively 120), and apply integrated metrics for performing an HLA-LOH classification on the received HLA allele-based coverage data.

In some examples, the process 100 includes analyzing the BAM files 102 and additionally retrieving unmapped/discarded reads (i.e., reads from a BAM file that are either assigned locations within HLA gene loci or flagged as unmapped). In some examples, such as process 200 shown in FIG. 3, the HLA and HLA-LOH analysis system executes a preprocessing script that formats the unmapped reads (and the HLA mapped reads) from the BAM files 104 and 106 into two FASTQ files, which are fed into the next process. For the two FASTQ files, one FASTQ file is generated and contains all of the forward reads from each paired-end read, while the other FASTQ file contains the reverse of each paired-end read. In one example, the pairs are listed in corresponding order in the files, so the first read in the first FASTQ file will be the pair of the first read in the second FASTQ file. In another example, both forward and reverse reads could be included in the same FASTQ file as alternating sequences that share a similar read name. In another example, single read sequencing data could be included in a single FASTQ, or paired reads could be considered independent, disregarding their forward or reverse status and included in a single FASTQ.

If genetic sequence data from a normal, non-cancerous specimen from the patient that provided the cancer specimen is not available, sequencing data from a panel of exemplary normal specimens may be used. In one example, sequencing data from the panel of normal specimens having HLA genetic sequences most similar to the patient's cancer sample may be selected to create an HLA-matched panel of normal specimens.

Figure 3:
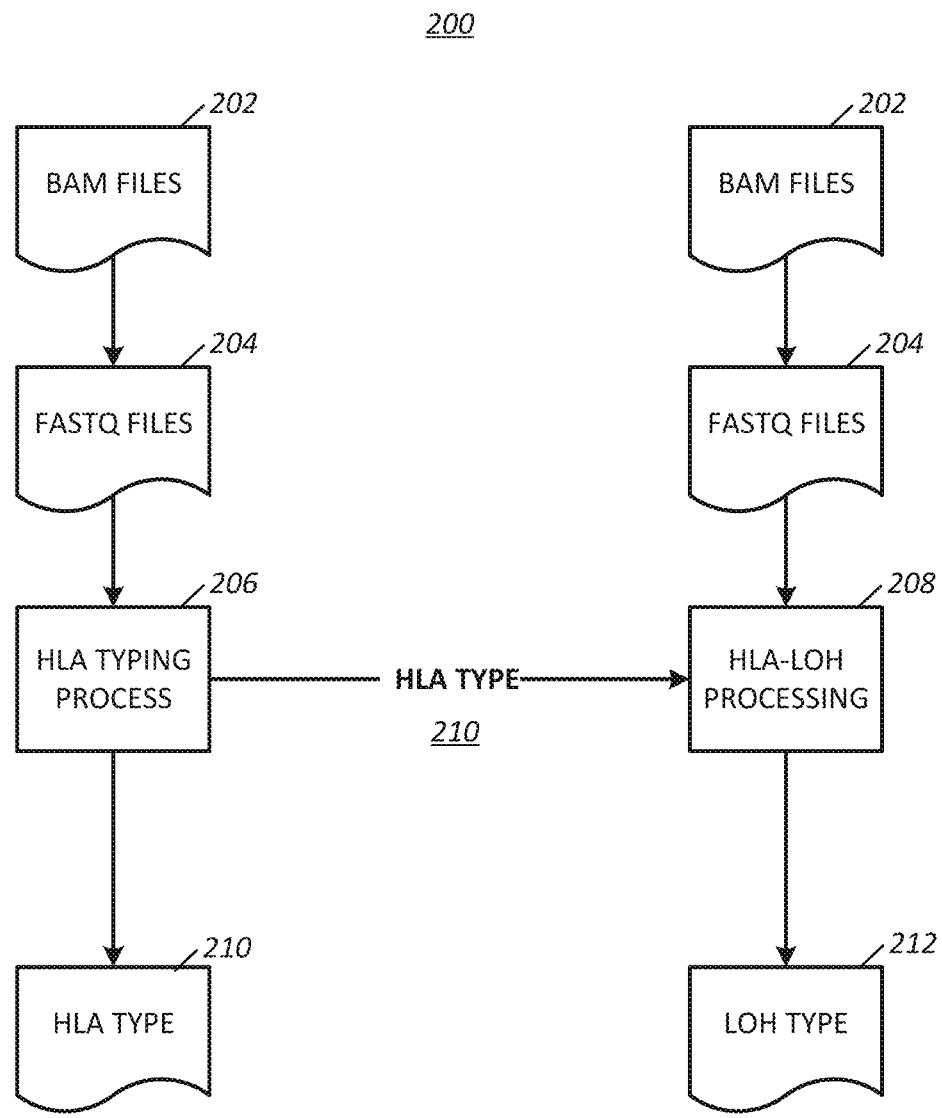
FIG. 3 illustrates an example process schematic for data flow for an HLA typing model and a loss of heterozygosity in HLA genes (LOH) model (collectively the HLA and HLA-LOH model).

FIG. 3 illustrates example process 200 for the data flow for the HLA typing and the HLA-LOH model that may be implemented through the process 100. In some examples, the two FASTQ files may be used for both HLA typing to generate HLA type, and for the LOH model, which also receives the HLA type/patient reference as input.

Initially BAM files 202 (such as files 102) are accessed on the HLA and HLA-LOH analysis system. These BAM files 202 may be stored on the system, generated from tissue and/or blood biological samples from a subject and from populations of subjects, or generated remotely and accessed by the system, for example, through a bioinformatics pipeline that includes network accessible NGS systems or databases. FASTQ files 204 are generated from the BAM files 202. The FASTQ files 204 may include a FASTQ file that contains all of the forward reads from each paired-end read, and another FASTQ file that contains the reverse of each paired-end read. In another example, the FASTQ files 204 may consist of a single FASTQ file that contains single end reads, or paired end reads that are being considered as independent reads. The FASTQ files 204 are provided to two different processes, an HLA typing process 206 and an HLA-LOH process 208. The HLA typing process 206 generates candidate alleles in the form of HLA type data 210 for the subject's sequence data in the BAM files 202 sample. The HLA-LOH process 208 generates HLA-LOH data 212 for the subject's sequence data. Each of the HLA type data 210 and the HLA-LOH data 212 may be stored by the HLA and HLA-LOH analysis system and reported to clinicians or other personnel.

To generate the FASTQ files 204, in some examples, e.g., using the process 112, an alignment is performed on the sequencing data in the BAM files 202, wherein the sequencing data is aligned against a reference genome. Further, the genetic positions indicating locations in the reference genome of mapped reads having a sequence that map to the reference genome is determined. Further still, unmapped reads in the next generation sequencing data are determined, as well, and the mapped reads data and unmapped reads data are stored in one or more FASTQ files 204 having sequence reads.

These sequence read FASTQ files 204 are fed to the processes 206 and 208. The process 206 identifies candidate HLA alleles and stores the candidate HLA alleles as the HLA type data 210 in an HLA reference file. In the example shown, the HLA type data 210 from the process 206 is additionally fed to the HLA-LOH process 208, which determines the HLA-LOH status for each identified HLA allele. The data 210 and 212 are then stored and a report of the HLA-LOH statuses for each of the HLA alleles may be generated.

For the HLA typing, in an example of the process 206, an HLA typing algorithm, which may include the Optitype HLA Typing algorithm (Szolek et al., OptiType: precision HLA typing from next-generation sequencing data, Bioinformatics 2014, which is hereby incorporated by reference and in its entirety for all purposes) or the Kourami HLA typing algorithm (Lee et al., Kourami: graph-guided assembly for novel human leukocyte antigen allele discovery, Genome Biology 2018, which is hereby incorporated by reference and in its entirety for all purposes), may be applied to the two FASTQ files 204 input to the HLA typing process. In an example, the HLA typing algorithm finds mapped reads (pairs of reads) and analyzes them to predict which HLA alleles the patient has. For example, the HLA typing algorithm generates a list of predicted HLA alleles for the sample, based on reads that map to either the original reference HLA or any known HLA genetic sequence, including those in the international ImMunoGeneTics (IMGT) database. In one example, the sequences of some of the most common Class I HLA alleles are well-characterized and available to download through the IMGT (imgt.org). In one example, there are at least 40,000 known HLA genetic sequences.

In an example, the Optitype HLA Typing algorithm is used. The Optitype HLA Typing algorithm works on the premise that the correct genotype explains the source of more reads than any other genotype, where an allele is said to explain a read if the read is aligned to it with no more mismatches than to any other allele. Hence, the HLA Typing algorithm finds an allele combination, which maximizes the number of reads they explain. The HLA Typing algorithm includes three main steps. First, reads are mapped against a carefully constructed HLA allele reference. Because only exon 2 and 3 subsequences are available for all alleles, these regions are considered during read mapping so that no allele is disadvantaged because of incomplete sequence information. Additionally, for exome and genome sequencing data, HLA Typing algorithm may include flanking intronic regions and a process to impute missing sequence data based on phylogenetic information. Second, from the initial read mapping results, a binary matrix is generated indicating which alleles a specific read could be aligned to with the least number of mismatches. Finally, based on this matrix, a special case of the set cover problem is formulated as an integer linear program (ILP) that selects up to two alleles for each locus simultaneously, maximizing the number of mapped reads that can be explained by the predicted genotype. Besides the major HLA-I alleles A, B and C, minor alleles G, H and J are considered during optimization, as long subsequences of these minor loci show high similarity with major loci, occasionally causing ambiguous read alignments.

In another example, the Kourami HLA typing algorithm is used. The Kourami HLA typing algorithm is a graph-guided assembly technique for classical HLA genes, which can construct allele sequences given high-coverage whole-genome sequencing data. The Kourami HLA typing algorithm takes advantage of partial-order graphs (POGs) to capture all known alleles. The Kourami HLA typing algorithm further modifies the graph to include variants found in the sequencing data so that the graph includes the paths of true alleles. We a comprehensive reference panel is created from a combined multiple sequence alignment (MSA) of both full-length and exon-only known alleles for each HLA locus. Reads mapped to all known HLA loci in the human reference genome are extracted and aligned to the comprehensive reference panel. Gene-wise POGs are constructed using the combined MSAs. The alignments of the extracted reads are projected onto the graphs so that each read alignment is stored as a path in the graphs and the read depths on the edges naturally become edge weights. When these read- or read-pair-backed paths connect two or more neighboring heterozygous sites of two alleles, they provide phasing information. During the alignment projection, the graphs are modified by adding nodes and edges to incorporate differences found by the alignment, such as substitutions and indels. Note that a sequence of an allele may be encoded as a path through the entire graph. Finally, using the weighted graphs with alignment paths, Kourami HLA typing algorithm formulates the problem of constructing the best pair of HLA allele sequences as finding the pair of paths through the graph. When finding the pair, the Kourami HLA typing algorithm considers consistent phasing information from the reads and coverage using base quality scores. Additionally, the pair of paths may be identical, to permit homozygous alleles.

Table 1 includes 150 examples of Class I HLA alleles.

TABLE 1

| HLA-A | HLA-B | HLA-C |
|---|---|---|
| A*01:01:01:01 | B*07:02:01:01 | C*01:02:01:01 |
| A*01:01:01:02N | B*07:02:01:02 | C*01:02:01:02 |
| A*01:01:01:03 | B*07:02:01:03 | C*01:02:01:03 |
| A*01:01:01:04 | B*07:02:01:04 | C*01:02:01:04 |
| A*01:01:01:05 | B*07:02:01:05 | C*01:02:01:05 |
| A*01:01:01:06 | B*07:02:01:06 | C*01:02:01:06 |
| A*01:01:01:07 | B*07:02:01:07 | C*01:02:01:07 |
| A*01:01:01:08 | B*07:02:01:08 | C*01:02:01:08 |
| A*01:01:01:09 | B*07:02:01:09 | C*01:02:01:09 |
| A*01:01:01:10 | B*07:02:01:10 | C*01:02:01:10 |
| A*01:01:01:11 | B*07:02:01:11 | C*01:02:01:11 |
| A*01:01:01:12 | B*07:02:01:12 | C*01:02:01:12 |
| A*01:01:01:13 | B*07:02:01:13 | C*01:02:01:13 |
| A*01:01:01:14 | B*07:02:01:14 | C*01:02:01:14 |
| A*01:01:01:15 | B*07:02:01:15 | C*01:02:01:15 |
| A*01:01:01:16 | B*07:02:01:16 | C*01:02:01:16 |
| A*01:01:01:17 | B*07:02:01:17 | C*01:02:01:17 |
| A*01:01:01:18 | B*07:02:01:18 | C*01:02:01:18 |
| A*01:01:01:19 | B*07:02:01:19 | C*01:02:01:19 |
| A*01:01:01:20 | B*07:02:01:20 | C*01:02:01:20 |
| A*01:01:01:21 | B*07:02:01:21 | C*01:02:01:21 |
| A*04:04:07:22 | B*07:02:01:22 | C*01:02:01:22 |
| A*01:01:01:23 | B*07:02:01:23 | C*01:02:01:23 |
| A*01:01:01:24 | B*07:02:01:24 | C*01:02:01:24 |
| A*01:01:01:25 | B*07:02:01:25 | C*01:02:01:25 |
| A*01:01:01:26 | B*07:02:01:26 | C*01:02:01:26 |
| A*01:01:01:27 | B*07:02:01:27 | C*01:02:01:27 |
| A*01:01:01:28 | B*07:02:01:28 | C*01:02:01:28 |
| A*01:01:01:29 | B*07:02:01:29 | C*01:02:01:29 |
| A*01:01:01:30 | B*07:02:01:30 | C*01:02:01:30 |
| A*01:01:01:31 | B*07:02:01:31 | C*01:02:01:31 |
| A*01:01:01:32 | B*07:02:01:32 | C*01:02:01:32 |
| A*01:01:01:33 | B*07:02:01:33 | C*01:02:01:33 |
| A*01:01:01:34 | B*07:02:01:34 | C*01:02:01:34 |
| A*01:01:01:35 | B*07:02:01:35 | C*01:02:02 |
| A*01:01:01:36 | B*07:02:01:36 | C*01:02:03 |
| A*01:01:01:37 | B*07:02:01:37 | C*01:02:04 |
| A*01:01:01:38 | B*07:02:01:38 | C*01:02:05 |
| A*01:01:01:39 | B*07:02:01:39 | C*01:02:06 |
| A*01:01:01:40 | B*07:02:01:40 | C*01:02:07 |
| A*01:01:01:41 | B*07:02:01:41 | C*01:02:08 |
| A*01:01:01:42 | B*07:02:01:42 | C*01:02:09 |
| A*01:01:01:43 | B*07:02:01:43 | C*01:02:10 |
| A*01:01:01:44 | B*07:02:01:44 | C*01:02:11 |
| A*01:01:01:45 | B*07:02:01:45 | C*01:02:12 |
| A*01:01:01:46 | B*07:02:01:46 | C*01:02:13 |
| A*01:01:01:47 | B*07:02:01:47 | C*01:02:14 |
| A*01:01:01:48 | B*07:02:01:48 | C*01:02:15 |
| A*01:01:01:49 | B*07:02:01:49 | C*01:02:16 |
| A*01:01:01:50 | B*07:02:01:50 | C*01:02:17 |

In an example, the HLA alleles identified are HLA-A Allele 1: A*02:01, HLA-A Allele 2: A*01:01, HLA-B Allele 1: B*07:02, HLA-B Allele 2: B*07:02, HLA-C Allele 1: C*07:01, HLA-C Allele 2: C*07:02. Further still, in some examples, the HLA typing algorithm generates an accession number, which allows the user to retrieve an allele sequence. The output from the HLA typing algorithm is provided to downstream HLA-LOH models, e.g., the process 208.

Returning to FIG. 2, in some examples, the process 100 uses the list of predicted HLA alleles, such as data 210, to create a preliminary HLA reference file composed of reference sequences of the patient's predicted HLA alleles and all HLA pseudogenes. In some examples, the HLA reference file is automatically generated. In some examples, the HLA reference file may be automatically generated by pulling sequences from the Optitype (github) source code, especially the Optitype database/reference library (including the IMGT dataset) or Kourami reference library based on allele and accession number, for example using a data converter to maintain allele nomenclature consistency.

In an example, predicted Class I HLA type data 122 is obtained and an HLA reference file is generated at a process 124, by adjusting to match the predicted HLA alleles of the non-cancer specimen. In various embodiments, the process 124 generates a patient-specific HLA reference file by writing the sequence associated with each of the patient's predicted Class I HLA types to a FASTA file. In one example, a FASTA file is essentially a text file where lines alternate between a sequence name (these lines start with a >symbol by convention followed by the sequence name, for example, HLA00001) and the following line is the nucleotide sequence corresponding to that sequence name. The process 124 writes the name and sequence for each predicted Class I HLA type as well as the pseudogenes. The output from the process 124 is an HLA reference file as a FASTA file that, in various embodiments, is then converted or indexed to a novoalign index file for alignment to generate a .nix file. In one example, the .nix file is a specialized format that allows novoalign software to more quickly and efficiently align reads. If the patient is homozygous for a given allele, it is included only once in the reference. This HLA reference file then may be a patient specific HLA reference file.

In various aspects, the HLA reference file is a sequence file that includes the patient's predicted HLA class I genes and all nonclassical HLA genes and HLA pseudogenes to ensure that a read maps to the correct gene, even though there is high homology from gene to gene. In some examples, the HLA reference file is expanded to include class II HLA genes.

A process 126 aligns HLA mapping reads, along with unmapped/discarded reads (from the two paired end FASTQ files mentioned above), to the predicted patient reference file (which is the FASTA file that has been indexed to be a .nix file), for example, using Novalign to generate a BAM file.

The process 126 may filter the BAM file (in one example by using pySAM) using various filtering criteria, such as, for example, checking that: (1) the read is properly paired, (2) the read is not qc_fail (failed by quality control checks), (3), the read is not a duplicate, (4) the edit distance to the reference sequence of the predicted allele is less than or equal to 2, (5) the read has less than or equal to 2 insertions compared to the reference sequence of the predicted allele, (6) the read has less than or equal to 2 deletions compared to reference sequence of the predicted allele, and/or (7) both ends of paired read must map to the same predicted allele. A filtered BAM file is generated as a result.

Next, the process 126 may apply a variant calling process performed on the filtered alignment file (for example, the filtered BAM file), using freebayes (available from github), to identify any nucleotide positions where the patient's HLA sequences diverge from the HLA reference. In an example, implementation of the variant calling included the following criteria: the sequence data must include at least 3 reads supporting the variant (indicating that the patient has an alternate allele, meaning a sequence that is not identical to the reference sequence of the predicted allele), and fewer than 5 reads supporting the reference sequence of the predicted allele.

Subsequently, a process 128 updates the patient specific reference by replacing portions of the reference sequences with the variant sequences that are supported by at least 3 reads at the genomic positions of those variants to generate an updated patient HLA reference file. In this way, the updated patient HLA reference sequence file has been adjusted to match the exact nucleotide sequence of the non-cancer specimen HLA genes. In one example, the sequence is contained in a FASTA file that is then converted to a novoalign index file. If the patient is homozygous for a given allele, the sequence is included only once in the reference.

The updated HLA reference file may then be sent to the process 112. In an example implementation of the process 122, a Novalign alignment of HLA mapping reads is repeated along with aligning unmapped/discarded reads to the updated reference file (if updates were made). Strict filtering may be used, including read is properly paired; read is not qc_fail; read is not a duplicate; edit distance to reference is 0; read has zero insertions to reference; read has zero deletions to reference; read is not mapped more than once. In other words, in an example, including only reads that have no edits, no indels (100% homology/no edit distance), and no multimapping (each read must map to one allele with a likelihood that is greater than 50%, do not allow one read to equally map to both alleles) to generate a non-cancer specimen BAM file.

In an example, for the cancer specimen data (i.e., the tumor HLA mapped reads 110), the process 112 aligns HLA mapping reads along with unmapped/discarded reads, to the patient HLA reference sequence (the updated HLA reference sequence data from process 128) using Novalign and filters reads with pySAM, using strict filtering criteria to generate a cancer specimen BAM file.

Next, the process 114 receives the aligned HLA mapping reads and data from the process 112 and calculates coverage (for example, the number of reads that map to a single nucleotide position) for normal HLA reads. In various embodiments, coverage may be inferred for nucleotide positions located between two appropriately-oriented paired reads, for example, if the two non-overlapping reads that comprise a paired-end read do not explicitly include a nucleotide position, but flank the nucleotide position, the presence of a molecule containing this intervening nucleotide position can be inferred, and thus the paired-end read may be included in the coverage metrics calculation for that nucleotide position. For example, this paired-end read would count as a read that maps to the nucleotide position even though the nucleotide position is located between the two ends of the paired-end read. In an example, the process 114 uses bedtools to assess coverage across each of the predicted HLA alleles in the non-cancer specimen BAM file. The result is a Table of Positional Coverage across each HLA allele in the non-cancer specimen. The process 114 generates a csv file (116) with the number of reads that uniquely map to a specific HLA allele at each nucleotide position along that allele in the non-cancer specimen. In one example, each column in the csv file represents a nucleotide position in an HLA gene and each row represents an allele. Each entry is a number representing the number of reads at that nucleotide position for that allele.

The process 114 further calculates coverage for tumor HLA reads, e.g., using bedtools to assess coverage across each of the predicted HLA alleles in the cancer specimen BAM file. The result is a Table of Positional Coverage across each HLA allele in the cancer specimen, generating a csv file (116) with the number of reads that uniquely map to a specific HLA allele at each nucleotide position along that allele in the cancer specimen. In one example, the positional coverage for both the non-cancer and cancer specimen are contained in one csv file. For example, row 1 may represent allele A in the normal sample, row 2 may represent allele B in the normal sample, row 3 may represent allele A in the tumor sample, and row 4 may represent allele B in the tumor sample. In one example, the cancer specimen is circulating tumor DNA (ctDNA) obtained from a blood sample and the coverage obtained from NGS analysis of ctDNA may differ from coverage obtained from NGS analysis of a specimen that contains solid tumor tissue or cancerous blood cells. The calculation of coverage metrics may be adjusted accordingly.

The process 114 combines data from the Table of Positional Coverage across each HLA allele in the non-cancer specimen and the Table of Positional Coverage across each HLA allele in the cancer specimen, to generate higher level features to describe relative changes in coverage between the non-cancer specimen and cancer specimen and a Combined Coverage Metrics Table (e.g., using formulae for calculating, one example may include formulae from the following Python packages: pandas, NumPy, SciPy).

This process 114 may generate a Combined Coverage Metrics Table, in the form of an expanded csv file that contains positional statistics on not only coverage depth but features including allelic frequencies of each allele, log ratios of each allele between tumor and normal, and areas of low sequencing coverage (See FIG. 9 for more details). The process 114 may also generate a Summary Statistics Table, in the form of a csv file where each row is an HLA gene and the columns contain summary statistics describing the differences in allele level coverage that will be used to make HLA LOH determinations.

Figure 4:
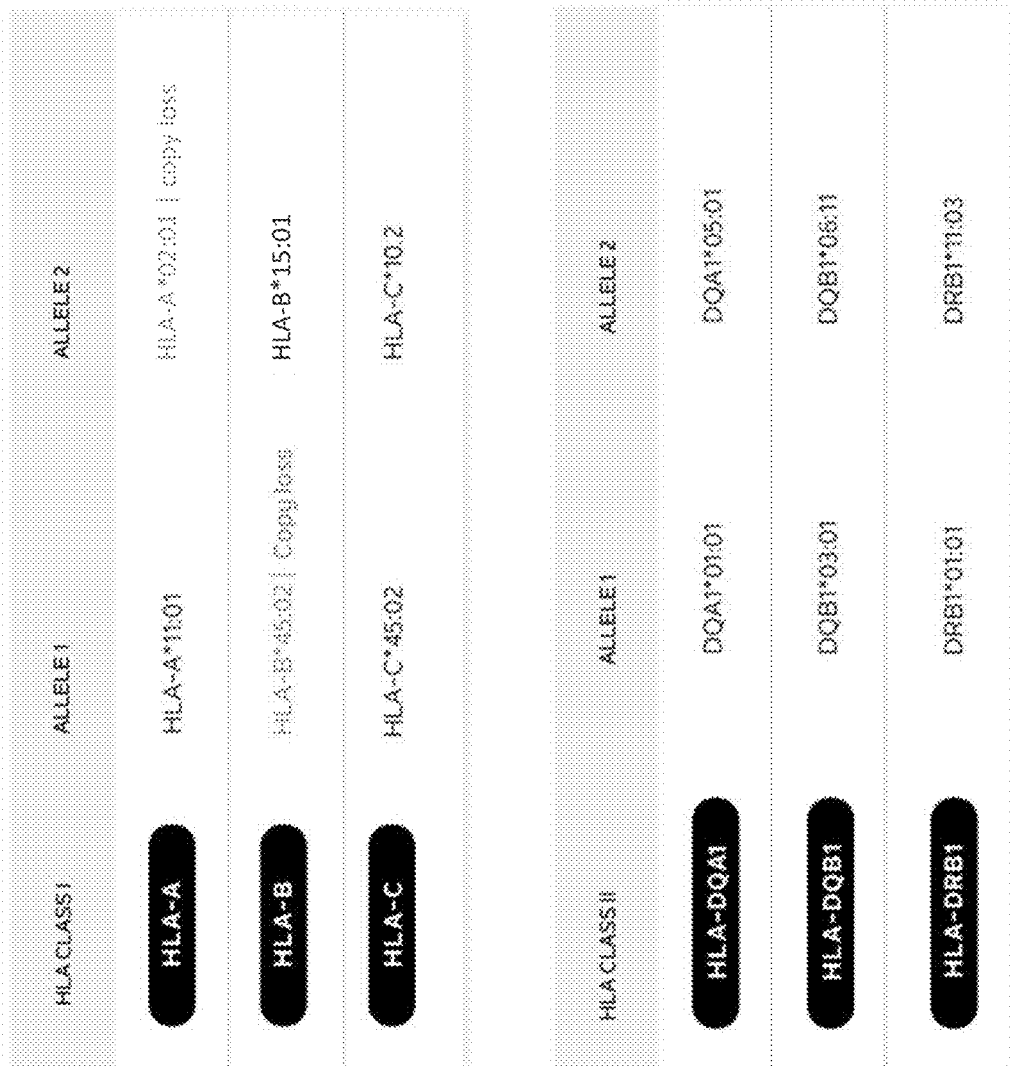
FIG. 4 illustrates an example HLA typing report, generated in an example.

FIG. 4 illustrates an example output report displaying the results of HLA-LOH classification. In this example, there are two detected copy losses (HLA-LOH) for HLA class I genes. For instance, an HLA-A allele (HLA-A*02:01) has been lost and an HLA-B allele (HLA-B*45:02) has been lost. No HLA-C alleles or HLA class II genes are reported lost in this example. All HLA alleles without the copy loss designation have been detected as present in the specimen.

The report may include information related to the lost or present HLA alleles, including clinical trials for which the patient is eligible, therapies that may match the patient and/or adverse effects predicted if the patient receives a given therapy, based on the present or lost HLA alleles in the patient's tumor. For example, the report may include information related to whether the patient's tumor is potentially-resistant to HLA-restricted immunotherapies. In this instance, because the HLA-A*02:01 and HLA-B*45:02 alleles have been lost, the report may state that the patient may not respond to immunotherapies based on those lost HLA alleles, may not be eligible for clinical trials listing those lost HLA alleles as inclusion criteria, and may be eligible for clinical trials listing those lost HLA alleles as exclusion criteria. On the contrary, immunotherapies based on any present HLA alleles may be matched to the patient and the patient may be eligible for clinical trials listing present HLA alleles as inclusion criteria, and may not be eligible for clinical trials listing present HLA alleles as exclusion criteria.

Figure 5A:
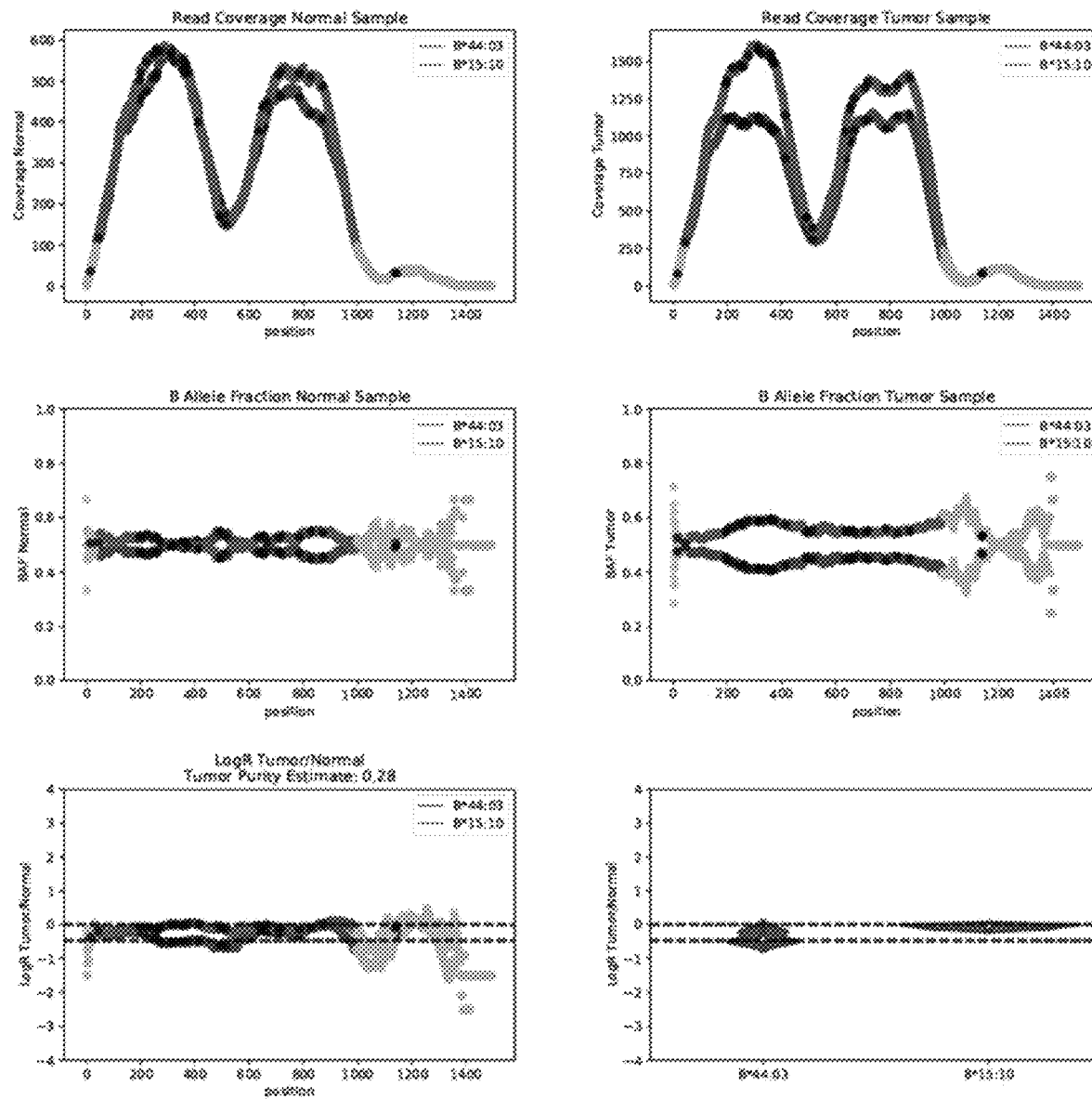
FIGS. 5A, 5B, and 5C collectively illustrate plots of coverage metrics calculated for different examples of the techniques herein, some in comparison to non-technique examples, and some without the filter steps. For example.
Figure 5B:
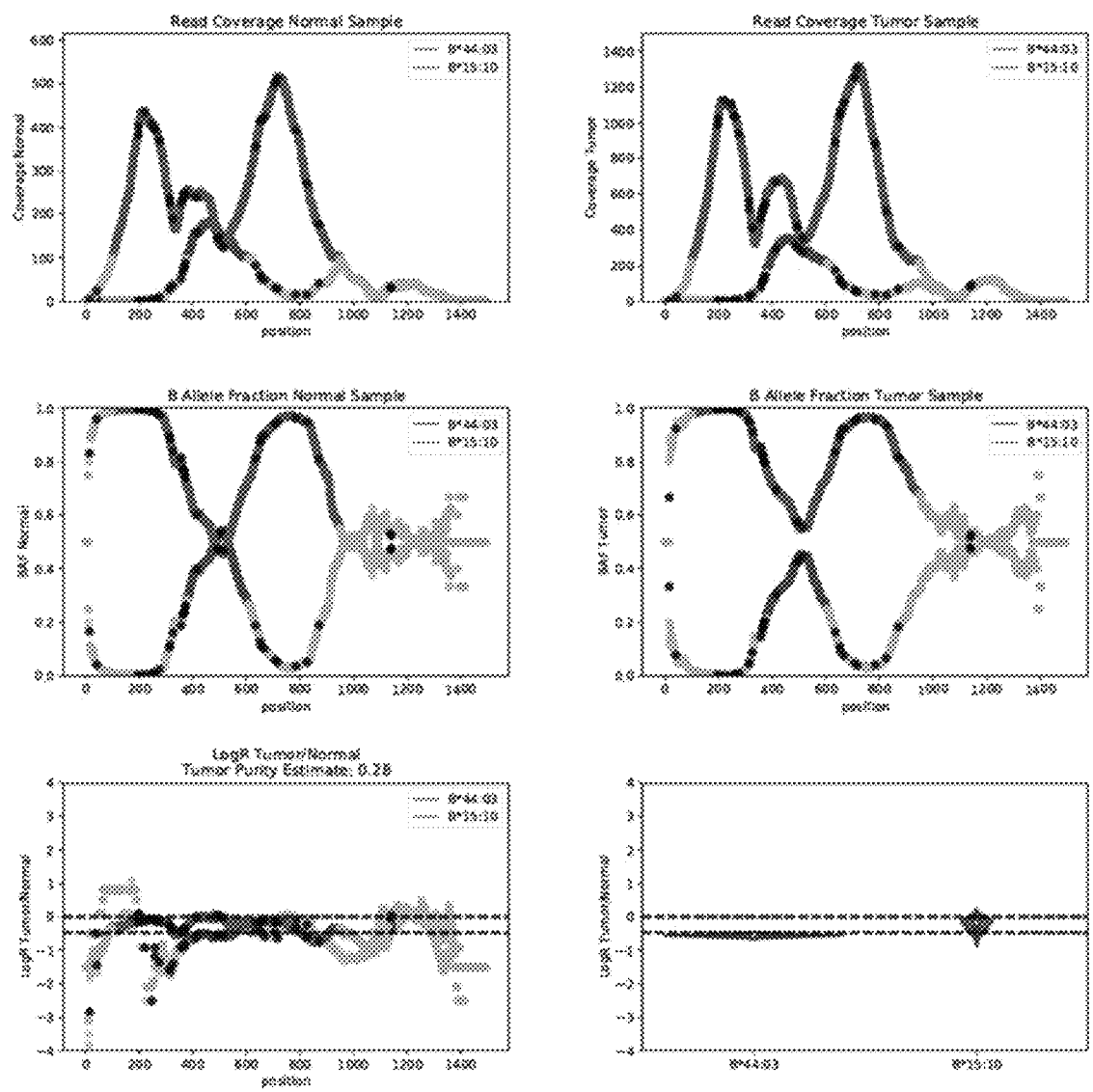
Figure 5C:
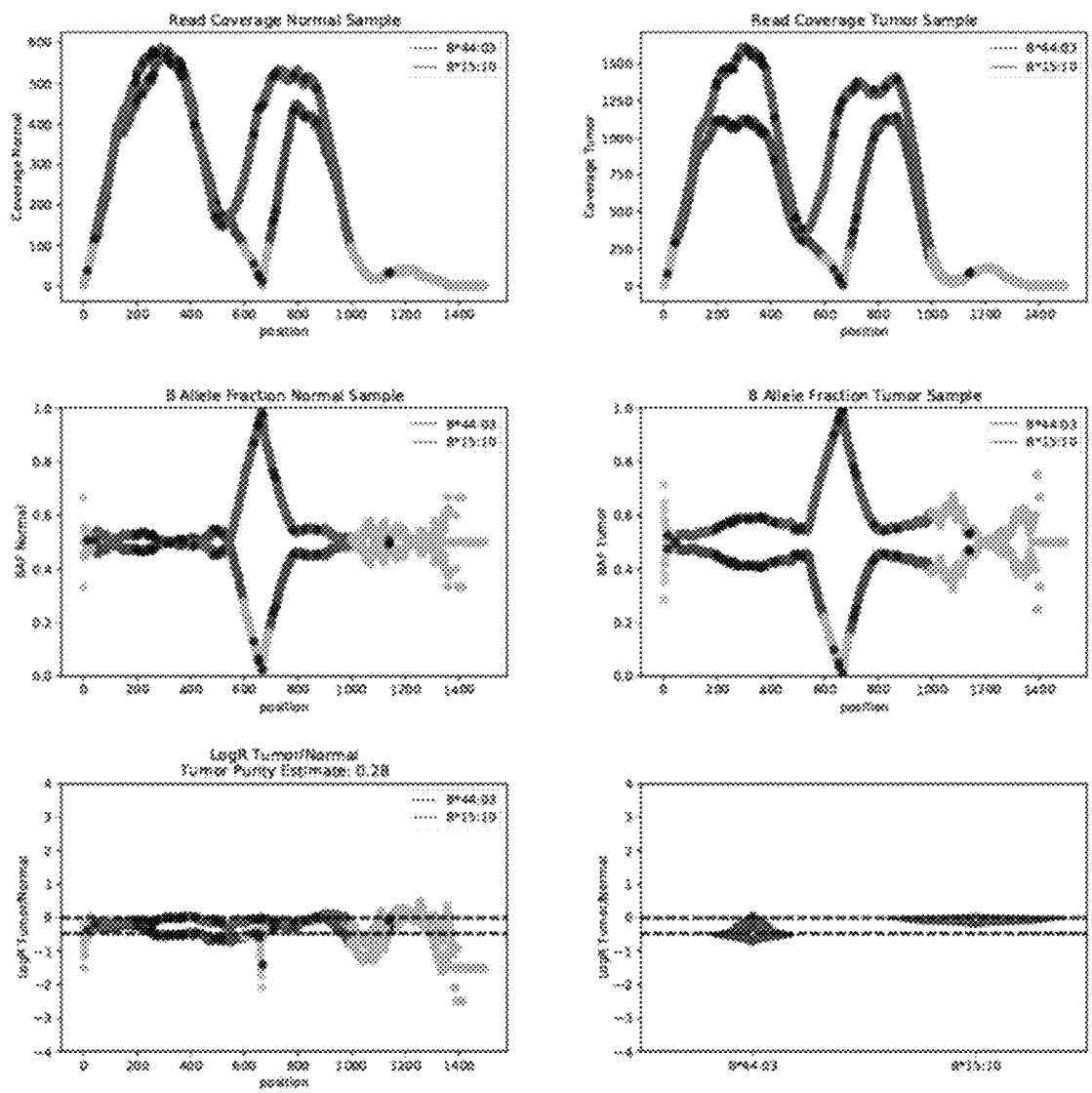

FIGS. 5A-5C are plots of combined coverage metrics for different examples of the techniques herein, some in comparison to non-technique examples, and some without the filter steps. (See, FIGS. 9A-9D for more details). For example, FIG. 5A shows data that were calculated using all disclosed steps and features, FIG. 5B shows data calculated without aligning discarded/unmapped reads to HLA genes, and FIG. 5C shows data calculated without replacing the HLA reference sequences with the variants detected in the sequence data generated by the patient sample.

With the Combined Coverage Metrics Table and Summary Statistics Table formed (116), at the process 118, the process 100 may determine and report LOH Status for each HLA allele in the cancer (tumor) sample, with reference to the non-cancer (normal) sample. In an example without a normal sample extracted from the same patient as the cancer sample, the process 118 may report all HLA alleles present in the tumor sample (known as stable alleles, versus lost alleles that are missing, absent, or detected with low coverage from the tumor sample) or, the process 118 may compare to a normal sample from at least one distinct patient, where the sample(s) may have matched HLA types similar to the HLA types in the tumor sample to control for sequencing bias caused by hybrid capture, GC content etc. In one example, the more pure a tumor sample is, the stronger and more easily detectable a signal will be for a lost allele. As tumor purity decreases, the signal becomes increasingly hard to distinguish from background noise.

In an example, the features from the Summary Statistics Table (116) are input into a machine learning classification model (of process 118) that returns a likelihood of LOH. In an example, alleles with a likelihood of LOH greater than 50% are reported as LOH.

Figure 6:
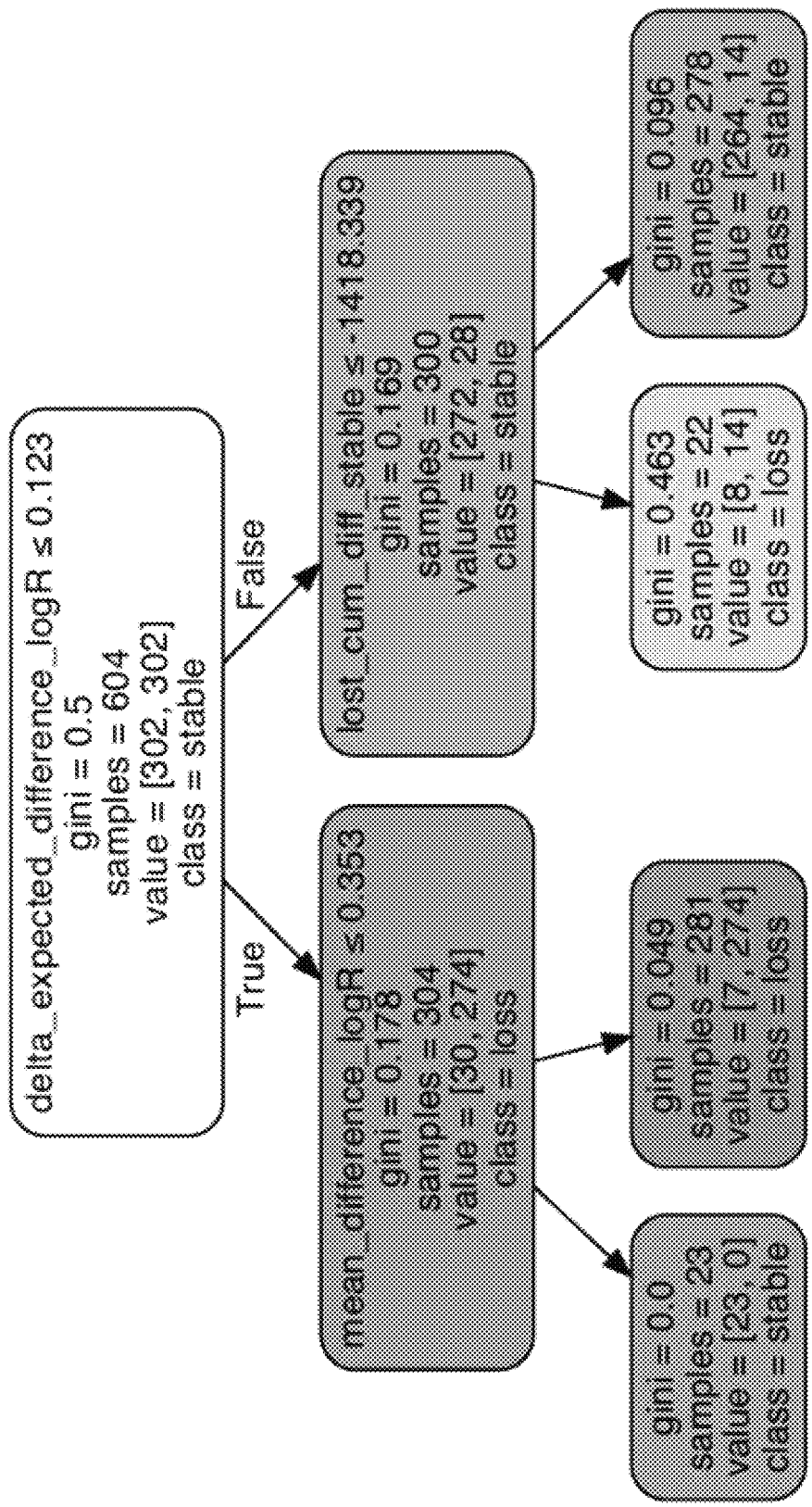
FIG. 6 illustrates an example shallow decision tree showing the use of coverage metrics to predict HLA-LOH.

In an example, LOH Status Predictions for each allele in the predicted HLA alleles are determined by the process 118 using a Shallow Decision Tree machine learning model. FIG. 6 illustrates an example shallow decision tree 300 that may be executed by the process 118. In one example, the first line of each node (represented by a box in FIG. 6) is the name of a feature that corresponds to a statistic selected from the Summary Statistics Table (116) and a cut-off threshold against which the sample's value for that feature is compared. If the value of the sample meets or does not meet the threshold criterion, the sample is sorted into the corresponding branch of the decision tree. For example, if delta_expected_difference_log R of a sample is less than or equal to 0.123, the mean_difference_log R of the sample is then compared to a set threshold, etc. The other lines of text in a box may indicate the gini index value for that node, the number of samples (which may mean the number of HLA genes that were analyzed for LOH) sorted by that node, and during model training, "value" may act as a confusion matrix by indicating the number of samples (HLA genes) that were sorted into that node and that had manual annotations of either loss (right number) or stable (left number) HLA status.

In one example, the decision tree 300 is shallow/short with few nodes to avoid overfitting, decisions are based on features from the Summary Statistics Table (116), and features or threshold values may change). In various examples, a decision tree that is shallow may be easier to interpret, making it easier to explain the classification of a patient or specimen, for example, if a physician calls to ask about a "borderline" allele. Thus, the classification models of process 118 may be particularly configured to reduce processing time and increase the speed by which particular alleles can be classified, for faster ultimate diagnosis. These decision tree models are also typically more resilient to variations in upstream sample analysis. If the decision tree is not as shallow, meaning there are more features, this may result in the model being more accurate and/or overfitted and the model may not correctly classify new data. In one example, decision tree outputs are more discrete, for example, three possible decision tree outputs could be clear loss of an HLA allele, or clear stability of an HLA allele, and one intermediate state. Another example may include more than one intermediate state. In other examples, LOH Status Predictions from the process 118 may be determined using other decisional techniques, such as Random Forest methods which may be slightly more accurate, and may yield a more continuous distribution of probabilities/likelihoods, for example, 75% likelihood of a loss of an HLA allele.

In an example, the process 118 may apply a coverage threshold, such that any HLA allele with coverage below a threshold is reported by the process 118 as a loss of heterozygosity for that allele. The process 118 may be configured such that the threshold may be specific to the testing panel used for NGS sequencing. For example, the coverage threshold below which an allele is reported as lost may be approximately 75 reads for an example (targeted ~600 gene) genomic sequencing panel or 35 reads for an example (whole exome) sequencing panel, where the process reports each allele as either stable or lost. The model may report an equivocal or uncertain status for an allele in a specimen that is not obviously stable (present in the specimen) or lost (absent from the specimen). In some examples, coverage metrics for an allele may fall in the middle of the distribution of coverage metrics values observed from all specimens, placing the coverage metrics in a range where the allele has a roughly equivalent probability of being either lost or stable.

In some examples, further reporting is performed. For example, the process 100 may match a patient with clinical trials and/or a therapy/therapies that are likely to eliminate the cancer cells, based on HLA alleles that are present in cancer sample as predicted by the HLA LOH model. This may help a physician make a therapy decision or identify a matched set of possible therapies or clinical trials in which the patient may participate. In one example, the clinical trials are matched to the patient's HLA LOH results based on the trials having inclusion/exclusion criteria based on the presence of specific HLA alleles in tumor or cancer cells.

Optionally, in some examples, a biological assay to test for the presence of any of the alleles (especially an allele reported by the algorithm to be lost from and/or not present in the tumor or cancer cells) is performed. For example, an assay, which may include fluorescence activated cell sorting (FACS), may be performed employing a number of antibodies, for example, one detecting HLA allele A*02, one detecting A*03, and one detecting B*07, to confirm the presence or the absence of various HLA alleles. Antibodies directed to other alleles are known in the art, and additional antibodies to detect other HLA alleles are in development.

Figure 8A:
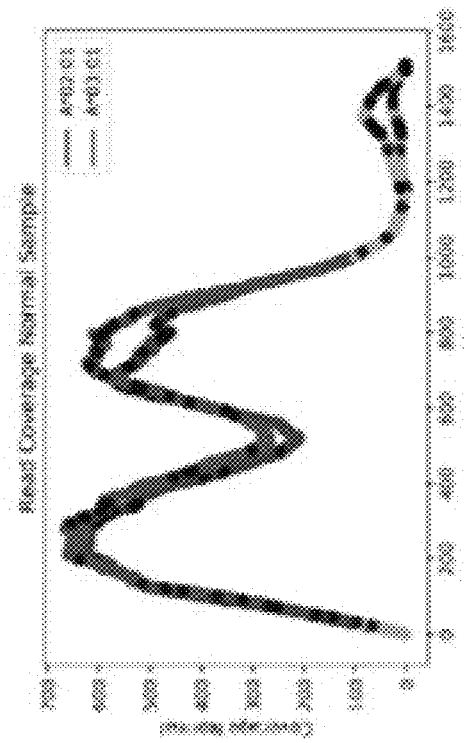
FIGS. 8A, 8B, and 8C collectively illustrate coverage metrics plots calculated by the methods disclosed herein for different types of tissues. In this example.
Figure 8B:
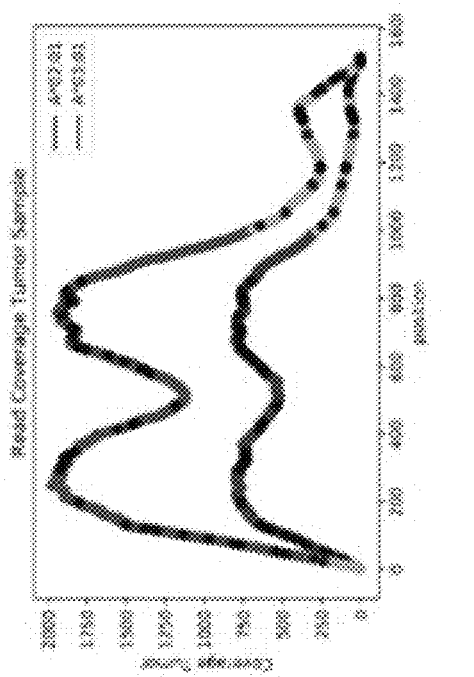
Figure 8C:
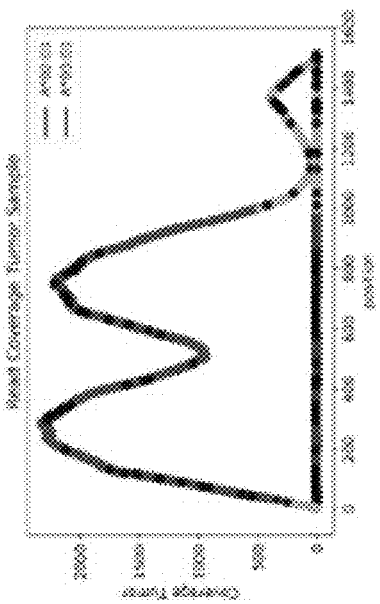
Figure 9A:
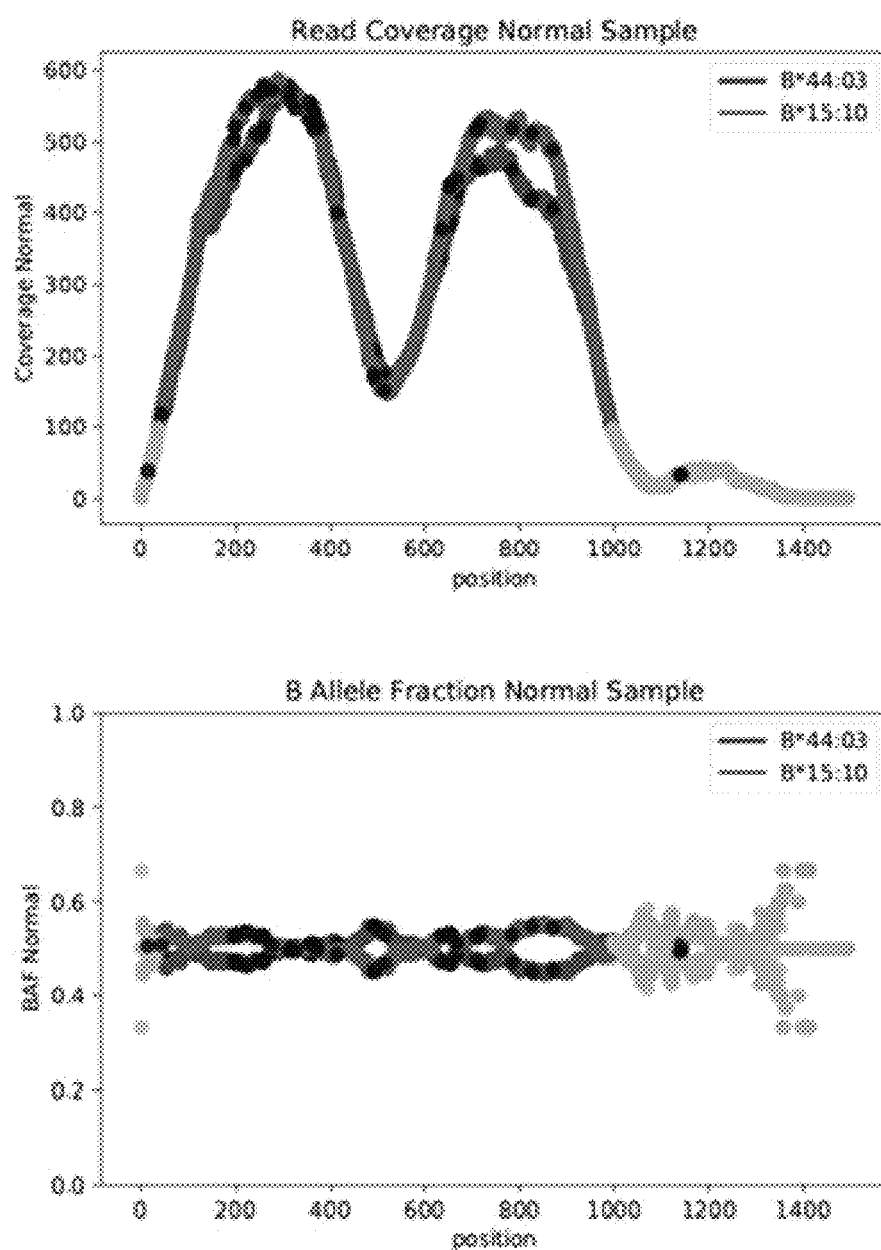
FIGS. 9A, 9B, 9C, and 9D collectively illustrate how various model features lead to more robust alignments and less noisy signal for downstream analysis by comparing plots of coverage metrics calculated for different examples of the techniques herein with coverage metrics calculated for non-technique examples, and some without the filter steps.
Figure 9B:
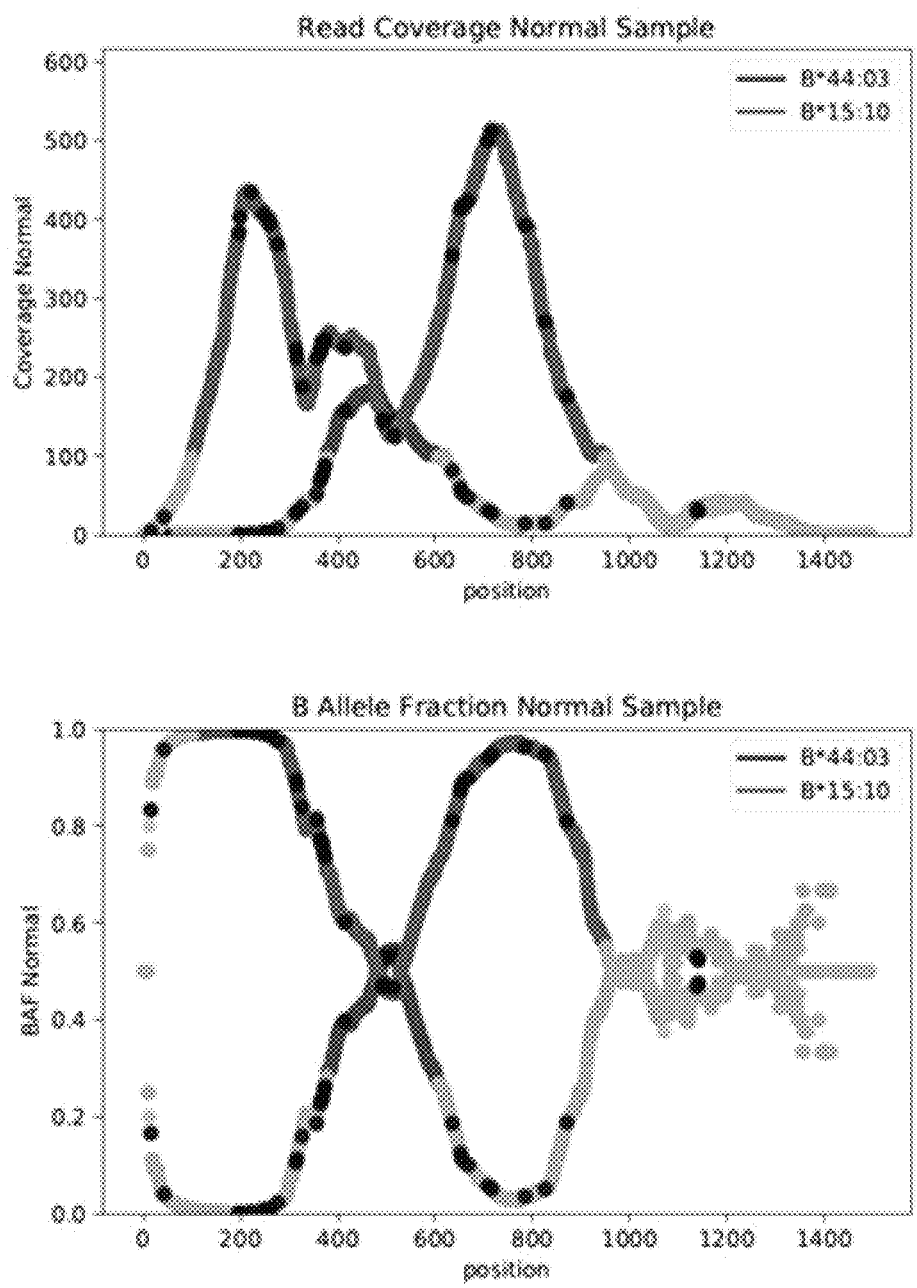
Figure 9C:
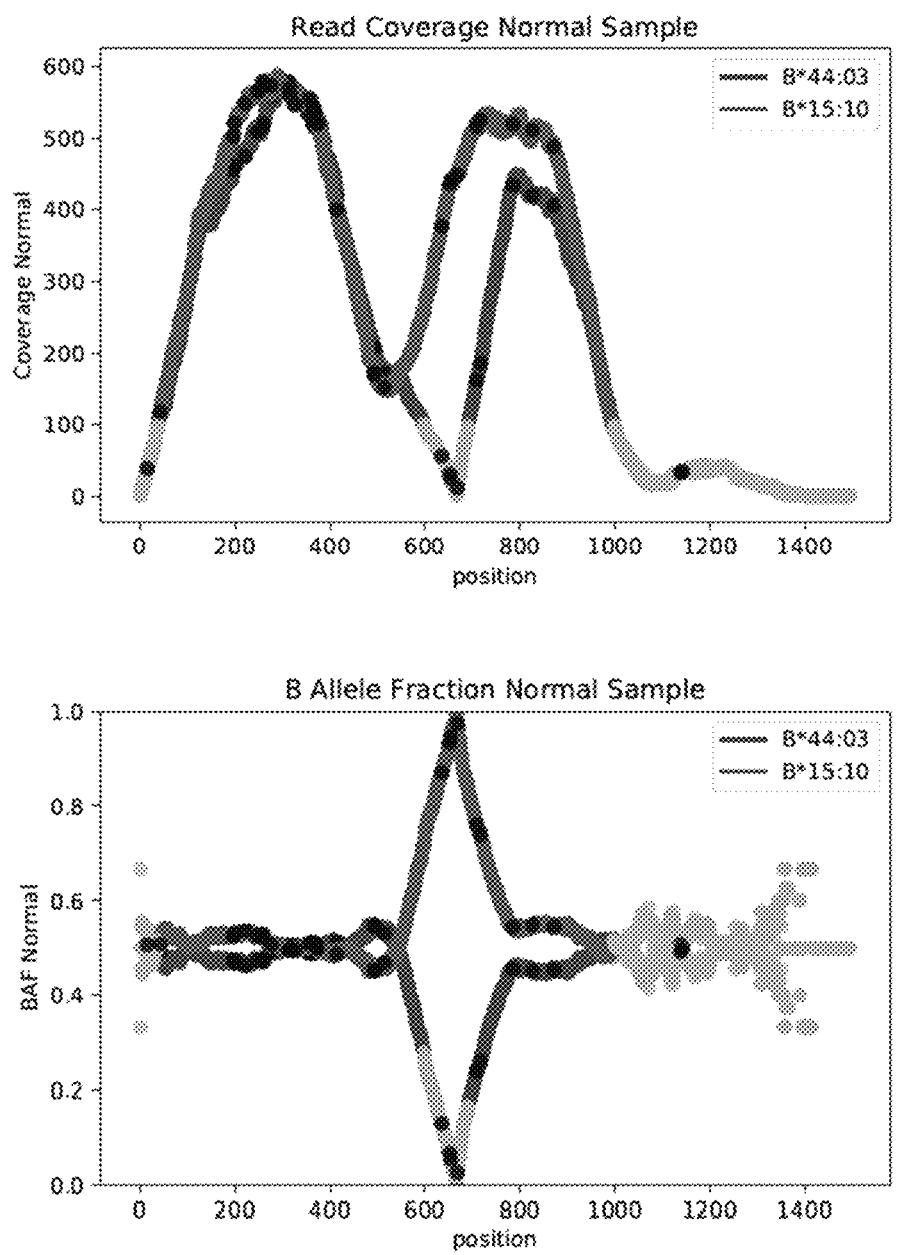
Figure 9D:
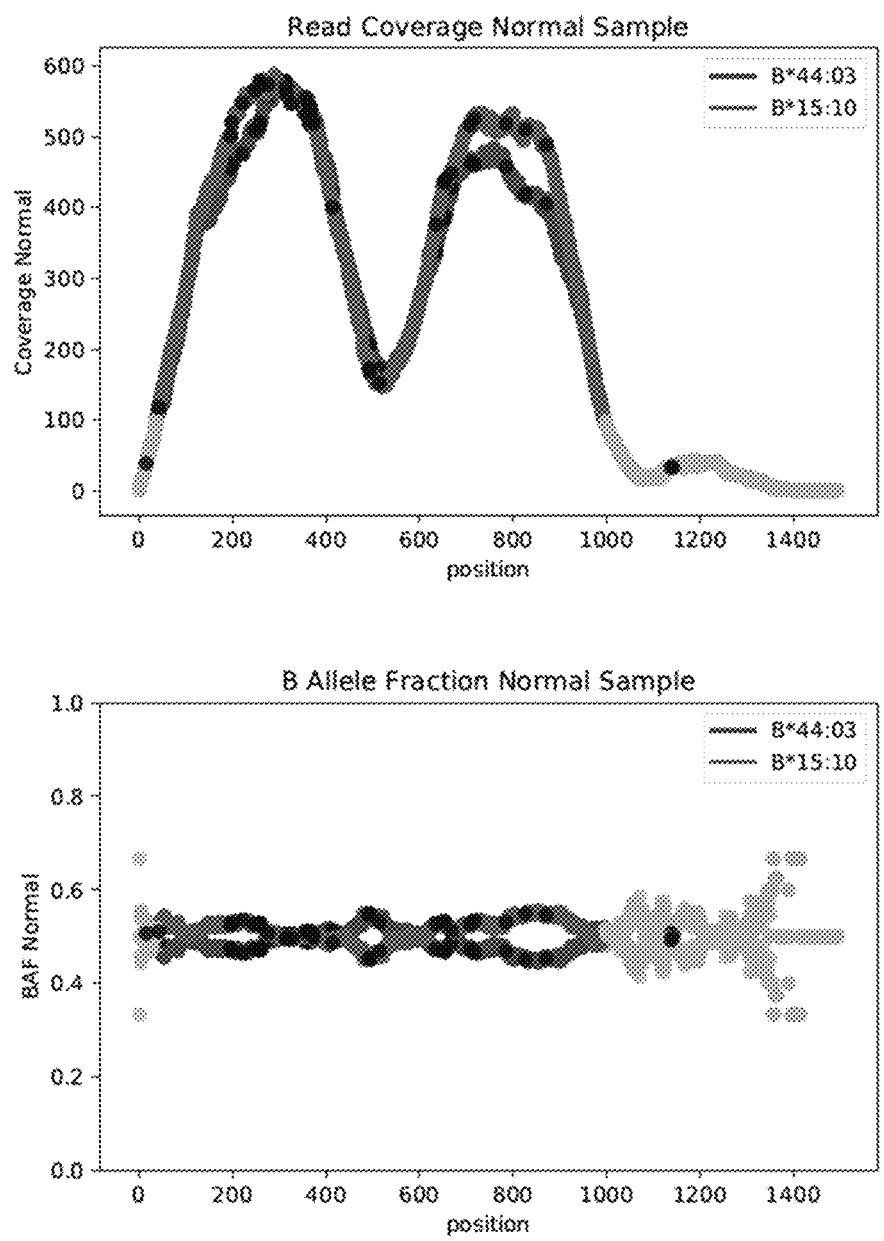

In this example, the techniques described herein were used to analyze a patient non-cancer sample, a patient cancer sample, and a tumor organoid (T.O.) derived from the patient cancer sample and predicted that the cancer sample and T.O. had lost an A*02 HLA allele but maintained a stable A*03 HLA allele (see FIGS. 8A-8C). To test that prediction, FACS was used on the T.O. to detect the presence of these two HLA alleles, and the results are shown in FIGS. 7A & 7B.

FIGS. 7A & 7B include the following FACS plots: the top row shows FACS results from an anti-A*03 antibody assay (FIG. 7A) and the bottom row shows FACS results from an anti-A*02 antibody assay (FIG. 7B). From left to right in each row, there is a plot for a negative A*02 control sample, a plot for the tumor organoid sample, and a plot for a positive A*02 control. The upper half of each plot indicates which cells bound the pan HLA Class-I antibody, indicating that those cells were expressing HLA Class-I molecules. The right half of each plot indicates which cells bound either the anti-A*03 antibody (top row) or the anti-A*02 antibody (bottom row), indicating that those cells expressed the allele targeted by the antibody used to generate that plot. Horizontal and vertical lines within the plots indicate the location of cut-offs used to determine those percentages and numbers in the outer corners of the plots indicate the percentage of all data points in the plot that are located in each quadrant of the plot.

Each of the plots shows a cell population that expressed HLA Class-I molecules, demonstrated by the data points being located in the upper two quadrants of each plot.

The A*02 negative control and the tumor organoid plots in the bottom row show a cell population that is not expressing the A*02 allele, demonstrated by the data points being located in the left two quadrants of the plots. All remaining plots show a cell population that expressed either the A*02 allele (bottom row plots) or the A*03 allele (top row plots), demonstrated by the data points being located in the right two quadrants of each plot.

Overall, this confirms that the prediction generated by the technique disclosed herein: that the tumor organoid contained a stable A*03 allele but had lost the A*02 allele.

It is noted that if fresh tissue is not available, a tumor organoid (T.O.) may be generated from a patient cancer cell sample, T.O. genetic material may be sequenced to generate T.O. sequence data, and the HLA LOH model may be used on the T.O sequence data. FIG. 8A-8C show examples of plots for different types of tissues. In this example, FIG. 8A shows coverage data calculated by the methods disclosed herein for the non-cancer sample tissue. FIG. 8B shows coverage data calculated by the methods disclosed herein for the cancer sample tissue. FIG. 8C shows coverage data calculated by the methods disclosed herein for a tumor organoid derived from the cancer sample tissue. FIG. 8A shows approximately equivalent coverage for two HLA alleles (A*02:01 shown in red data points and A*03:01 shown in blue data points) in the non-cancer tissue. FIG. 8B shows reduced coverage for the A*02:01 allele. The sequence reads from the cancer tissue mapping to the A*02:01 allele may be explained by the presence of non-cancer cells in the cancer sample due to the heterogeneity of cancer samples that do not have 100% tumor purity. FIG. 8C shows a complete loss of coverage for the A*02:01 allele. The complete loss of the A*02:01 allele in the T.O. may reflect the absence of non-cancer cells in the T.O., which indicates that the T.O. has 100% "tumor purity".

FIGS. 9A-9D illustrate example plots of coverage (number of reads) on the y-axis (plots in the top row) or the fraction of cancer specimen coverage divided by non-cancer specimen coverage (B allele fraction) on the y-axis (plots in the bottom row). These data are plotted for two HLA alleles (plotted as data points having either shades of red or shades of blue, depending on which allele is associated with each data point) at each nucleotide position indicated by the x-axis. In this example the two alleles are B*44:03 (red data points) and B*15:10 (blue data points). In one example, lighter shades of red or blue indicate that coverage at that nucleotide position was below a user determined threshold and data corresponding to reads mapping to those positions were excluded from downstream summary statistic calculations.

Each title ("Full Featured," "No Unmapped Reads," "No Update to Patient HLA Reference," or "No Pseudogenes in HLA Reference") indicates if a step of the technique disclosed here was skipped to achieve the data represented in the plots below the title, demonstrating the effect of that step on coverage.

Compared to the Full Featured plots in the left column, the coverages represented in the No Unmapped Reads plots were calculated without including discarded/unmapped reads during the step of aligning reads to HLA genes. In this example, calculated coverages appear to be misleadingly lower, especially for the B*44:03 allele.

Compared to the Full Featured plots in the left column, the coverages represented in the No Update to Patient HLA Reference plots were calculated without replacing the HLA reference sequences with the variants detected in the sequence data generated by the patient sample. In this example, calculated coverages appear to be misleadingly lower for the B*44:03 allele.

Compared to the Full Featured plots in the left column, the coverages represented in the No Pseudogenes in HLA Reference plots were calculated without tailoring the HLA reference sequences to the variants detected in the sequence data generated by the patient sample. In this example, calculated coverages appear to be similar, which may be explained by the HLA genetic sequences of the patient not being similar to known HLA pseudogene sequences. However, in another example, if the patient's HLA genes had sequences similar to HLA pseudogenes, coverages could appear higher because sequence reads may be incorrectly assigned as mapping to HLA genes when they actually would map to pseudogenes if the pseudogene sequences were included in the HLA reference.

There are a number of features of the present techniques, including, but not limited to the following:

Use of unmapped reads—during routine mapping of NGS reads to the reference genome (hg19) reads that fail to meet predefined mapping quality thresholds are stored at the end of the alignment file as unmapped reads. Due to the complex nature of the HLA locus, many of the reads that would map to the HLA genes will end up as unmapped reads due to either a high number of mismatched bases or a high degree of multimapping. As a result, the unmapped reads section contains a wealth of potentially informative and highly useful reads. The instant method is superior to previous methods by utilizing these previously discarded reads.

Using four-digit HLA type as an input—because the output from the Optitype algorithm does not provide a personalized HLA sequence for the sample in question, it is important to ensure that the reference sequence used for alignment fully matches the HLA sequence of the sample, which may include the steps of calling variants and updating the patient HLA reference to replace reference sequences with detected variants. The variant calling process may be facilitated by using a reference sequence that is as close as possible to the patient's sequence. The present techniques can take advantage of the finely curated IMGT dataset that is provided by Optitype (the same software used to perform HLA typing). This can have several advantages. For example, the Optitype dataset is optimized to have consistent sequence lengths across each allele, inferring missing intronic sequence when missing, which reduces the need to normalize LOH signal across sequences of highly divergent lengths (e.g., if one allele is 1400 bp and the other is only 400 bp).

Adaptive realigning to match patient reference—due the high degree of polymorphism in the HLA locus, it is important to be able to account for germline differences from reference sequences that may arise in a given HLA sequence in an individual. In some examples, the present technique first performs an alignment step using the patient's normal NGS data allowing for some degree of mismatch. By performing variant calling against the initial HLA reference, positions where the NGS data does not support the initial chosen reference can be identified. The reference can then be updated and the alignment repeated with the more appropriate reference sequence.

Inclusion of all of the sample's HLA genes in the mapping reference—while HLA genes are highly polymorphic, they are also highly homologous to one another. Of the Class I HLA genes, HLA-A and HLA-C are the most divergent, and yet still most alleles of these two genes share greater than 90% homology with one another across their most polymorphic regions (Exons 2 and 3). Because of this homology, including all of the patient's alleles in the mapping reference ensures that reads do not erroneously cross map between HLA genes or multimap to two HLA genes and skew coverage metrics.

Inclusion of pseudogenes in the mapping reference—In addition, there are a number of HLA pseudogenes (HLA-H, HLA-J, . . . HLA-Z, etc.) with potential homology to HLA-A, HLA-B, and HLA-C. To ensure that reads are properly assigned to the appropriate HLA gene and allele, these different genes are included in the reference comparisons in the instant methods. Otherwise, relative coverage could be skewed (see, FIGS. 9A-9D).

Use of unique HLA read counts in the remapped alignments of reads (including previously unmapped reads) as a normalization factor (match factor) between the Normal and Tumor Sample—in some examples, the Loss of Heterozygosity determination may hinge on whether there is a relative loss of coverage for a particular HLA allele in a tumor sample, relative to its matched normal control. This calculation may include normalizing the read counts between normal and tumor NGS data when they may have been sequenced at different depths. The metric used for normalization may include the number of unique reads mapping to the HLA reference, total reads, total mapped reads, or total mapped reads minus duplicates.

Use of information about positions that do not mismatch—an advantage of NGS sequencing approaches (relative to sanger sequencing) is that sequencing information is not strictly positional. It is possible to extract information not just about the abundance of a nucleotide at a specific position, but also information about the rest of the 150 bp paired end read that contributed to each observation of that nucleotide. By leveraging this feature, HLA allele specific coverage can be estimated at positions where the two HLA alleles actually have identical nucleotides.

Including read depth as a filtering feature—In order to build a method that performs optimally on a range of samples whose sequencing depth may vary, it is valuable to set a filtering threshold on which positions will be used for subsequent analysis. Without this filtering, the coverage features may get extremely noisy and will make accurate and precise LOH calls difficult (though not impossible given the disclosure herein). We have implemented a coverage feature that ensures that we only assess positions where we are confident in our coverage across both normal alleles (see, FIGS. 9A-9D).

Using Area based metrics rather than net scores—using area-based metrics rather than just the difference between values at mismatched positions has a number of different implications for the behavior of the method. For example, in this case, power of the method to distinguish LOH is less related to the number of mismatched positions. While samples with very high homology between two alleles of the same HLA gene may be difficult to resolve by NGS, as long as there is a minimal amount of divergence, the coverage across the entirety of the two alleles can be resolved. In other methods, a sample where the alleles diverge by 30 nt, will be more likely to be called LOH relative to one where they only diverge by 10 nt. This is not necessarily the case with the method described herein. Power to distinguish LOH is more of a function of coverage and estimates of tumor purity. In addition, these area-based metrics, when integrated with depth and coverage features, also incorporate some measure of how confident the model is in its ability to resolve the two alleles (e.g. a higher area-based score means there are more positions that meet the read depth threshold and diverge between the two alleles).

Using Area between Log R as a feature—Log R is the log 2 ratio of the read coverage in the tumor sample, divided by the read coverage in the normal sample, normalized by a match factor. When a sample has LOH the log R between the two alleles across the length of the HLA gene will be different, and in particular, the log R of the lost allele will significantly decrease. Calculating the cumulative area between the two log R lines for a pair of alleles, defined in this patent as the "observed difference in log R," provides increased sensitivity for detection of LOH.

Using the difference in area between the VAF curves as a feature—the B allele frequency (BAF) at any given position is the ratio of reads supporting each allele. The area between the two BAF curves defines how much the NGS reads have been skewed towards a particular allele. In cases where there is evidence of strong LOH, the BAF is almost 1.0 and 0 for the stable and lost allele, respectively. Thus, the tumor specific difference in BAF is an incredibly sensitive metric of allele loss. However, it is important to also normalize for any differences in coverage that may occur in the normal sample. In a normal sample, the BAF will fluctuate across the length of a gene but generally land somewhere around 0.5 for each allele, however it is not impossible for one allele to be slightly more well covered than the other (possibly due to better homology with sequencing probes). By subtracting this baseline coverage, the method arrives at a feature that is robust to noise and still very sensitive to allelic imbalance.

Calculating an expected difference in log R value based on tumor purity may be determined as follows. Tumor samples that are prepared for sequencing by NGS are generally heterogeneous and contain a mixture of tumor cells, healthy stroma and immune cells. As a result, a fully clonal loss may not necessarily appear as full loss of one allele sequence. For the sequencing specimen, it is advantageous to account for tumor purity when determining how much loss would be expected. Tumor purity may be estimated by methods that include but are not limited to assessing a histopathological slide corresponding to the sample that was sequenced by NGS, by analyzing DNA sequence data, or by analyzing RNA sequence data. Expected difference in log R may be defined as log 2 of (1—tumor purity).

Calculating delta_expected_difference_log R. An area-wise difference between the observed difference in log R value and the expected difference in log R value for a complete LOH sample, defined in this patent as delta_expected_difference_log R, may be determined by comparing the observed difference in log R to the expected value generated by our tumor purity estimate, the method more effectively determines whether the loss of HLA reads observed in the tumor sample represents a loss that would be on par with clonal LOH.

A loss of heterozygosity in a specific HLA gene (such as HLA-A, HLA-B, or HLA-C) in a cancer specimen may be determined in accordance with a threshold value, which may be set if, for instance, a significant difference exists between the read counts of the first tumor allele for the HLA gene and the read counts of the second tumor allele for the HLA gene. A significant difference may exist, for instance, if the difference between the read counts of the first tumor allele for the HLA gene and the read counts of the second tumor allele for the HLA gene is significantly more than the difference between the read counts of the first normal allele for such HLA gene and the read counts of the second normal allele for such HLA gene. "Significantly more" may be confirmed, for instance, when the delta_expected_difference_log R value for the HLA gene is significant. For instance, the delta_expected_difference_log R value may be significant if it is between 0 and −2. "Significantly" more may be confirmed, for instance in circumstances where LOH is partial rather than complete, when the delta_expected_difference_log R value for the HLA gene is between 0 and 0.1, between 0 and 0.2, between 0 and 0.25, between 0 and 0.5, or between 0 and 1.

Using predictions from neighboring genes to inform LOH decision—clonal HLA LOH almost always occurs as LOH in all three adjacent HLA genes. The methods described herein also account for this by adjusting LOH predictions based on the predictions of the neighboring HLA genes.

Determination of whether an HLA gene suffers a LOH can help further determine whether certain treatment options may be appropriate for patients. When it is determined that the cancer in the subject does not have a loss of heterozygosity in the HLA gene, treating the cancer by administering a therapy known to be effective against HLA-heterozygous cancers may be appropriate. For instance, a checkpoint inhibitor therapy may be appropriate for a subject with an HLA-heterozygous cancer. The checkpoint inhibitor therapy may be selected from the group consisting of an anti-CTLA-4 therapy, an anti-PD-1 therapy, or an anti-PD-L1 therapy, for example. Examples may include ipilimumab, nivolumab, pembrolizumab, pidilizumab, atezolizumab, Ipilimumab, and/or tremelimumab, and may include combination therapies, such as nivolumab+ipilimumab. As another example, a cancer vaccine may be appropriate, such as a cancer vaccine targeted to a specific HLA allele. One example is a peptide cancer vaccine available through Shiga University to treat HLA-A*02-positive advanced non-small cell lung cancer (NCT01069640). Another example is a peptide cancer vaccine available through Shiga University to treat HLA-A*24-positive advanced small cell lung cancer (NCT01069653).

FIG. 10 illustrates an example system 400 for HLA and HLA-LOH analysis that may be implemented on a network accessible processing system for performing the processes described herein. The system 400 may be part of a precision medicine platform. The example system may be part of an NGS system or implemented on one or more network accessible processing systems (e.g., servers) communicatively coupled to an NGS system, a network accessible sequencing database, digital reporting system, or other processing system.

The HLA and HLA-LOH analysis system 400 may be configured for performing the methods described herein including those of processes 100 and 200. The system 400 may include a computing device 402, and more particularly may be implemented on one or more processing units 404, e.g., Central Processing Units (CPUs), and/or on one or more or Graphical Processing Units (GPUs) 406, including clusters of CPUs and/or GPUs. Features and functions described may be stored on and implemented from one or more non-transitory computer-readable media 408 of the computing device. The computer-readable media 408 may include, for example, an operating system 410 and software modules, or "engines," that implement the methods described herein, including those of processes 100 and 200 and other processes illustrated and described herein.

The computer-readable media 408 stores an HLA analysis system 412 for performing the HLA typing processes and HLA-LOH processes described herein. In the illustrated example, the HLA analysis system 412 includes an HLA typing process 414 and an HLA-LOH process 416, both similar to those described in examples of FIGS. 2 and 3. An HLA-LOH report generator 418 is configured to store and generate HLA allele predictions and LOH allele reports, also in accordance with the examples herein.

More generally, the computer-readable media 408 may store sequence data processing instructions, including BAM file analysis instructions, sequence data filtering instructions, FASTQ file generation instructions, and normalization processes instructions for implementing the techniques herein. The computing device 402 may be a distributed computing system, such as an Amazon Web Services cloud computing solution. The computing device 402 may be implemented on one network accessible processing device 450 or distributed across multiple such devices 450, 452, 454, etc.

The computing device 402 includes a network interface 420 communicatively coupled to network 422, for communicating to and/or from a portable personal computer, smart phone, electronic document, tablet, and/or desktop personal computer, or other computing devices for communicating overlay maps, predicted tile classifications and locations, predicted cell classifications and locations, etc. Such information may also be stored in a database 424. The computing device 402 further includes an I/O interface 426 connected to devices, such as digital displays 428 for displaying generator overlay maps, user input devices 430, etc. A dashboard generator 432 may be used to generate GUI and/or other digital displays allowing a user to review and interact with and adjust generated HLA allele reports and HLA-LOH allele reports.

The network 422 may be a public network such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The computer-readable media 408 may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device may represent a CPU-type processing unit, a GPU-type processing unit, a field-programmable gate array (FPGA), another class of digital signal processor (DSP), or other hardware logic components that can be driven by a CPU.

Example 1

Methods: A total of 434 colorectal or non-small cell lung cancer samples underwent DNA sequencing on a genomic sequencing panel using paired, FFPE tumor and normal (blood or saliva) samples. To detect HLA-LOH from NGS data, we took advantage of accurate NGS-based HLA typing to resolve the patient's most likely HLA haplotype. Based on this haplotype, we adaptively realigned reads, extracted a number of features that describe the relative allele coverage in the tumor and normal sample, and used these features to make a confident determination of allelic loss in the patient's tumor sample.

Results: We found evidence of HLA-LOH in 16.32% of non-small cell lung tumor samples and 17.65% of colorectal tumor samples. We did not observe a significant association between LOH status and tumor mutational burden or neoantigen load. In the colorectal cancer cohort, we observed HLA-LOH in tumor samples that were classified as microsatellite instability high (MSI-H); however, the association between HLA-LOH status and MSI status was not statistically significant in this example.

Conclusions: We have developed novel techniques for determining HLA-LOH by NGS DNA sequencing, and demonstrate that, with the present techniques, HLA-LOH may now be detected in human tumors. Our results highlight the complexity of antigen presentation, the potential importance of HLA-LOH as a biomarker of immunotherapy response and resistance, and lays the groundwork for future investigations. Moreover, because the specific variety (allele) of HLA molecules presented by a patient's cancer cells may affect how the patient responds to various cancer treatments and may be an exclusion or inclusion criterion for clinical trials, the present techniques used for detecting/predicting loss of heterozygosity for HLA genes (HLA LOH) can be quite useful in guiding therapy decisions. The present techniques may also help pharmaceutical companies better understand why subsets of patients do and don't respond during a clinical trial.

Example 2

Background and Introduction: To investigate the prevalence of HLA-LOH, we utilized the specialized pipeline described above to detect HLA-LOH by DNA next-generation sequencing (NGS). Class I HLA alleles are highly polymorphic and most individuals have two distinct alleles for each HLA gene. Each allele allows for presentation of a unique pool of short peptides (approximately 8-11 amino acids in length) derived from the cellular products being made by each cell in the body. When an HLA allele has the capacity to present a peptide derived from a tumor-derived somatic mutation, this is known as a neoepitope.

Figure 11:
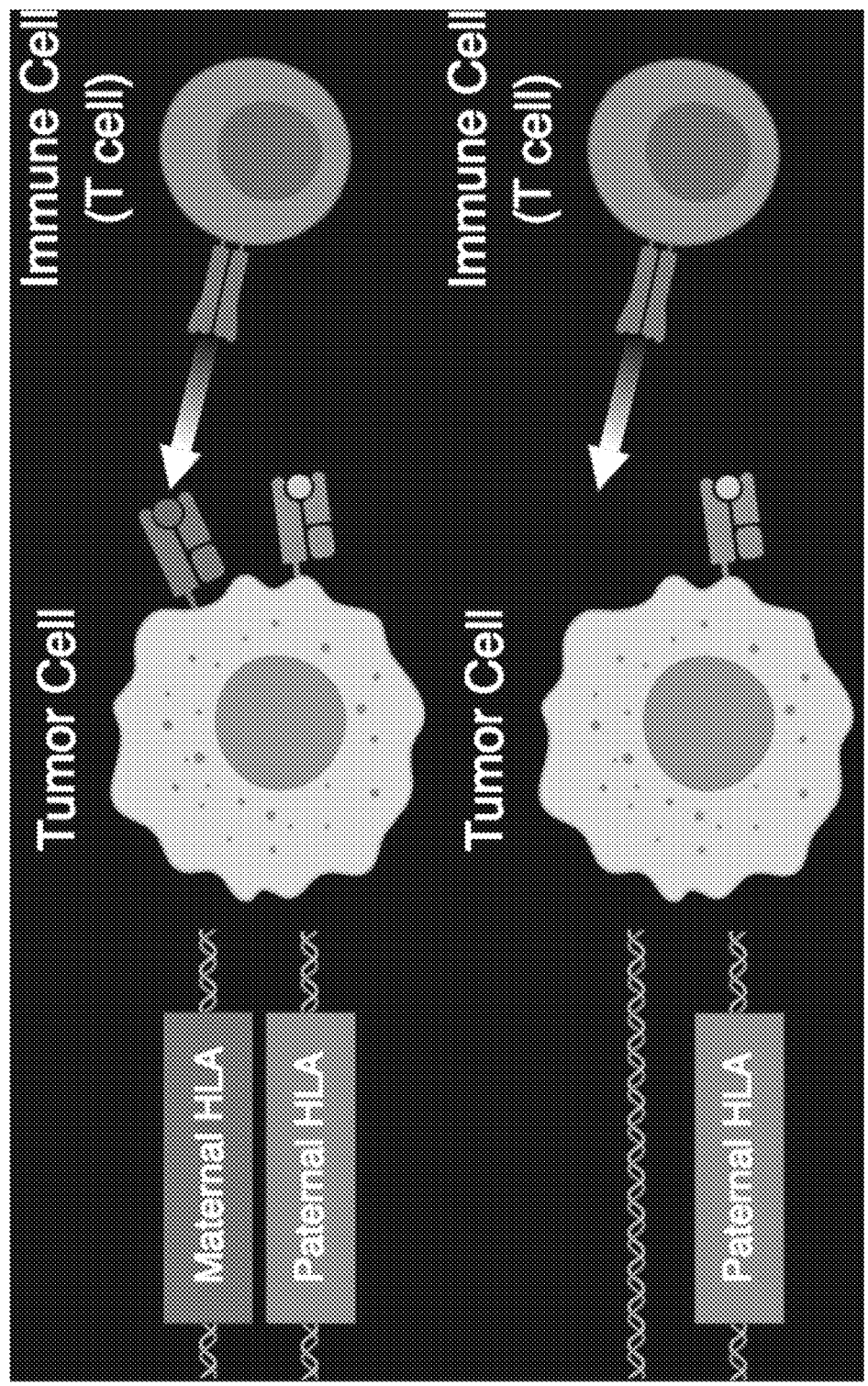
FIG. 11 illustrates how HLA-LOH can potentially lead to escape of immune pressure.

HLA Loss of Heterozygosity is a potential escape mechanism for tumors under immune pressure, where tumors can lose one copy of HLA and thereby avoid presenting potent neoepitopes. (See FIG. 11 and Tran et al., New England Journal of Medicine 2016; McGranahan et al., Cell 2017; Chowell et al., Science 2018)

As immunotherapies become increasingly targeted to specific tumor targets, HLA LOH could be an especially important escape mechanism to identify in target populations.

Methods: General Approach. The HLA-LOH process 100 was used. The HLA-LOH process 100 takes as inputs BAM files 102 from a matched Tumor and Normal Sample, respectively, as well as two digit HLA type 122 (similar to those generated by Optitype/Kourami/etc.), and tumor purity and ploidy information 120. (See FIG. 2) A full length HLA sequence is not required.

The process 100 then maps all HLA mapping reads as well as all unmapped reads to a new HLA reference 124 & 126. After accounting for potential germline variants present in the sample's HLA genes, it updates alignments and determines allele specific coverage.

By comparing changes in coverage between alleles, in the context of the expected tumor purity, the process 100 then determines, at 128, whether any reduction in allele coverage is consistent with a clonal loss of a specific HLA allele.

The output of the HLA-LOH process 100 is a prediction of LOH status for HLA-A, HLA-B, and HLA-C genes.

Method Development:

Leveraging Tumor Normal Sequencing—Because we perform paired-tumor normal sequencing in this example, we are able to leverage the relative HLA coverage in the patient's normal sample to serve as a reference for the expected coverage in an HLA stable tumor.

Figure 12:
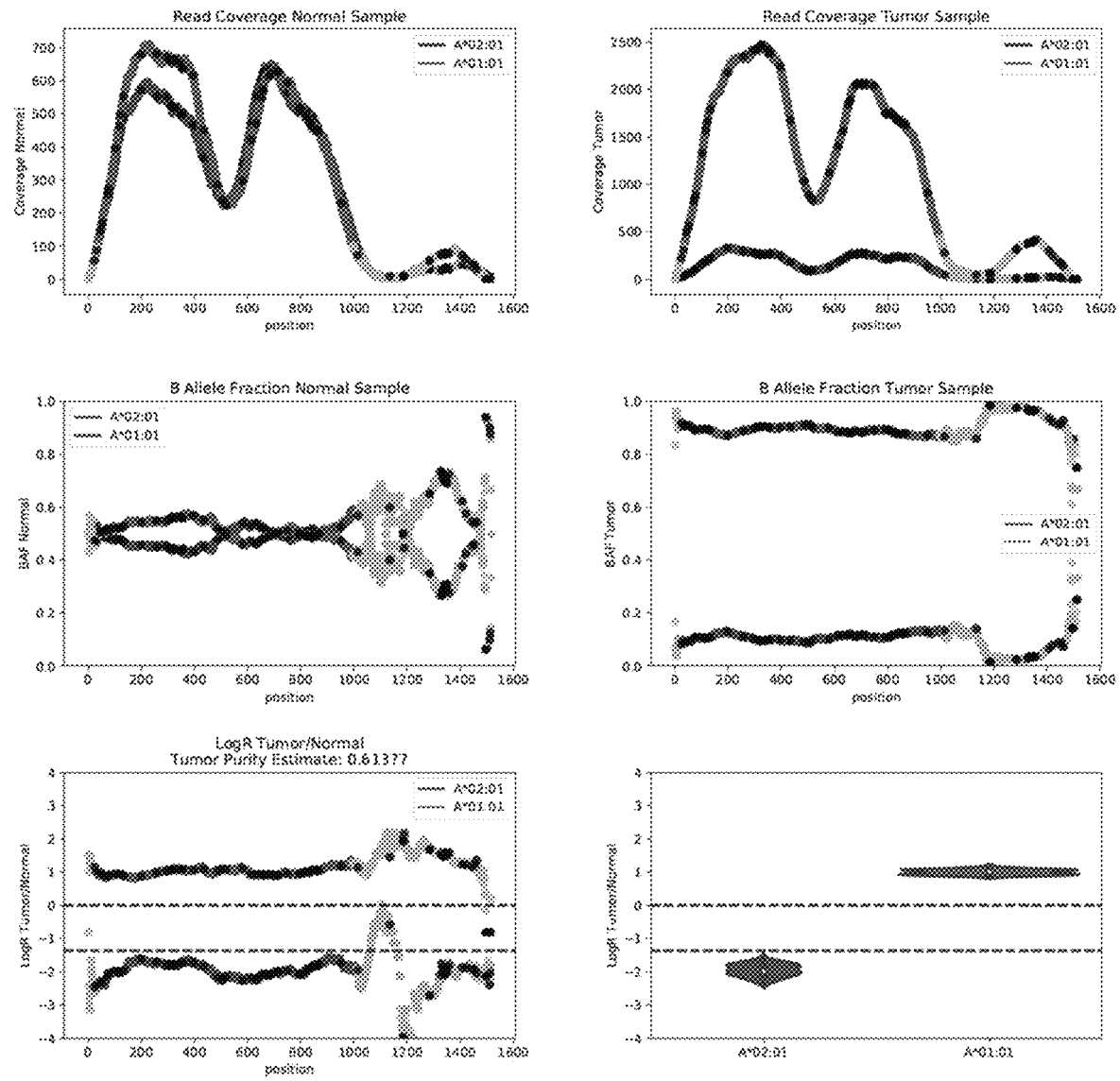
FIG. 12 illustrates relative differences in allele coverage metrics calculated in order to detect HLA-LOH, including B allele frequencies (BAF) and Log Coverage ratios, between the Tumor and Normal sample. The cancer specimen analyzed for these results represents a strong HLA-LOH. The allele predicted to have been lost and the allele predicted to be stable are highlighted in red and blue, respectively. Light colors (light blue and light red) indicate areas of low coverage and black dots indicate positions where the sequences of the two alleles diverge from one another.

Positional Feature Generation—Once we have allele specific coverage, we then calculate higher order features that help us describe the relative differences in allele coverage. These include B allele frequencies (BAF) and Log Coverage ratios between the Tumor and Normal sample (See FIG. 12).

Gene Feature Generation—The initial intuition is to think that we can only distinguish the two HLA alleles at nucleotides where they differ in sequence. However, because these alignments are based on much longer NGS reads we can actually infer the allele of origin for reads mapping to bases where the two alleles are identical, based on the presence of distinguishing polymorphisms elsewhere in the read.

Model Improvements and Advantages of this Model—The core of the algorithm hinges on accurately identifying HLA mapping reads and correctly assigning them to one of the patient's HLA alleles. As such, we are careful to control for any potential germline variation the patient may have from the reference HLA sequence, or potential cross-mapping caused by pseudogenes. Finally, because many aligners have trouble correctly aligning HLA reads due to the high degree of homology, we also rescue HLA reads from the unmapped reads pool (See FIGS. 9A-9D).

Results:

The prevalence of HLA LOH across cancer types—We first wanted to assess the relative prevalence of HLA LOH across a range of different cancer types. To address this we ran our HLA LOH algorithm on Tempus' recently published pan-cancer xT 500 cohort (Beaubier et al., Nature Biotechnology 2019).

Overall, we found that prevalence varied between different cohorts, with Lung and Colorectal cancer having the highest rates of LOH and Prostate and Brain having the lowest (See FIG. 13)

Figure 14:
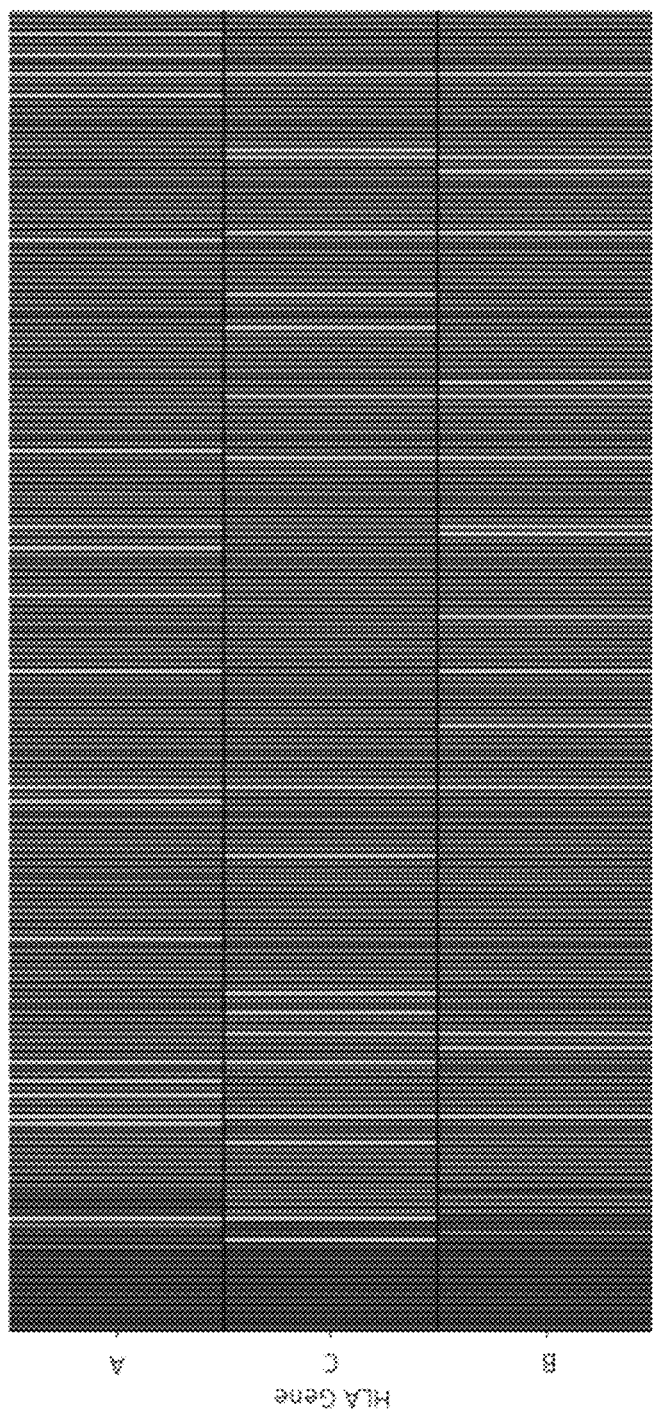
FIG. 14 illustrates predicted HLA-LOH status among all samples in the xT 500 cohort. Each column represents a sample, with the LOH status of each HLA gene (HLA-A, HLA-B, or HLA-C as denoted by the y-axis label) shown as Predicted LOH (red), Predicted Stable (blue), or Homozygous (grey).

HLA LOH occurs across the entire locus—We next wanted to better understand the nature of LOH in these samples. One feature that stood out was the fact that in the majority of cases (44/80), when LOH was observed at one gene in the HLA locus it was also observed across the other genes in that locus (HLA-A, HLA-B, and/or HLA-C genes), suggesting that the Class I locus is often lost together (See FIG. 14).

Figure 15:
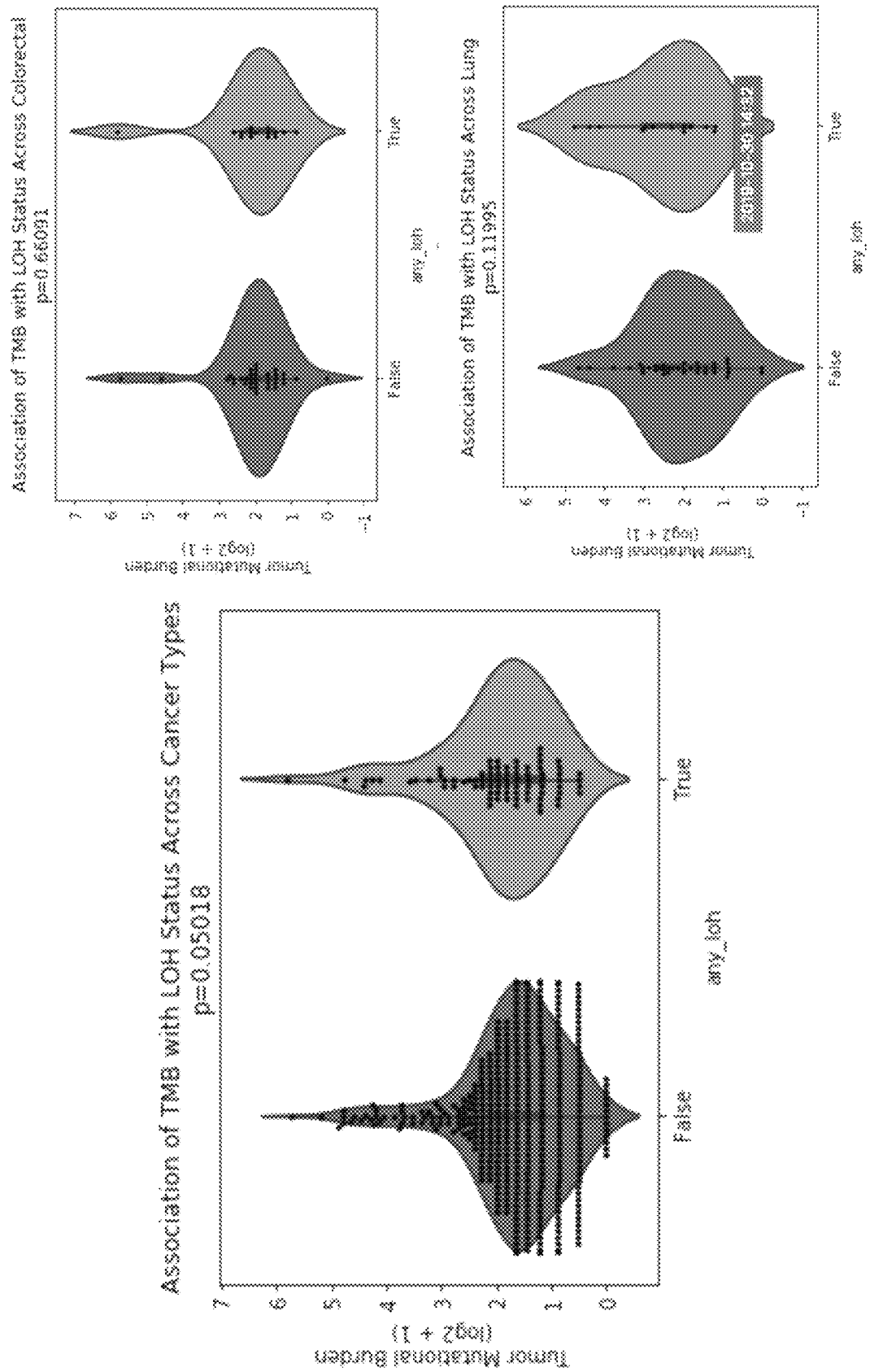
FIG. 15 illustrates the association or lack of association between Tumor Mutational Burden (TMB) and LOH status. These charts compare the log normalized TMB between samples with no HLA-LOH (blue) and predicted HLA-LOH (red). Significance was determined by Student's T test.

Association between HLA LOH and TMB—Given the use of Tumor Mutational Burden (TMB) as a pan-cancer metric for assessing tumor antigenicity, we were curious whether samples with high TMB would be more likely to undergo HLA LOH. In this example, there was a weak association between HLA LOH and TMB. Given the previous observation that certain cancer types in this cohort (for example, lung and colorectal) have a higher prevalence of HLA LOH, and those cancer types are known to have higher TMBs on average, it is possible that this association is mainly being driven by that effect. When we look more closely at the association within cancer type the association is less pronounced or absent. (See FIG. 15)

Validation of Model Results by Biological Assay:

We wanted to confirm that our LOH algorithm was identifying a biologically relevant LOH event. From our internal library of tumor derived organoids, we were able to identify a tumor organoid with very strong LOH (See FIGS. 8A-8C, an experimental design to confirm HLA LOH NGS results. Overview of HLA LOH NGS data for Normal sample, Original Tumor, and Tumor-derived Organoid).

As a first pass, we used our HLA LOH model to assess the LOH by NGS in both the healthy control (See FIG. 8A), bulk DNA sequencing of the tumor (See FIG. 8B), and tumor-derived organoid sequencing (See FIG. 8C). While we still detect residual A*02:01 signal in the bulk sequencing, the A*02:01 reads are almost entirely absent in the organoid, likely due to an absence of healthy normal tissue.

Because there is an antibody clone that can specifically detect the lost A*02:01 allele (BB7.2) we could actually confirm that this predicted LOH resulted in a loss of HLA-A*02:01 protein expression on the tumor-derived organoid.

Staining of the organoid sample, relative to control PBMC populations found that while the tumor-derived organoid retained strong expression of A*03:01, expression of A*02:01 was no longer detectable. (See FIGS. 7A and 7B, which are flow cytometry experiment results showing the expression of the stable and lost allele relative to a pan HLA antibody. Gated on live cells.)

We developed a method of determining HLA-LOH by DNA NGS and demonstrated that HLA-LOH is a detectable feature in human tumors, using our algorithm disclosed here.

By assessing HLA LOH across a range of cancer types from a published cohort, we find that there is variability in the prevalence of HLA LOH across different cancer types.

While there may be some pan-cancer association between HLA-LOH and TMB, further analysis must be done to determine the nature of the interaction.

Using flow cytometry we can confirm that the signal detected by the algorithm results in a biologically-relevant loss of protein. (See FIGS. 7A through 8C)

These results highlight the complexity of antigen presentation, the potential importance of HLA-LOH as a biomarker of immunotherapy response and resistance, and lays the groundwork for future investigations.

In processes herein implementing machine learning classifiers, a machine learning algorithm (MLA) or a neural network (NN) may be trained from a training data set. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where certain features/classifications in the data set are annotated) using generative approach (such as mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, long short term memory networks, or other neural models where the training data set includes a plurality of samples and RNA expression data for each sample. While MLA and neural networks identify distinct approaches to machine learning, the terms may be used interchangeably herein. Thus, a mention of MLA may include a corresponding NN or a mention of NN may include a corresponding MLA.

Training may include identifying common expression characteristics shared across RNA gene expressions in tissue normal samples, primary samples, and metastatic samples, such that the MLA may predict the ratio of a metastases tumor from the background tissue and identify which portion of an input RNA expression set may be attributed to the tumor and which portion may be attributed to the background tissue. Common expression characteristics may include which genes are expected to be overexpressed, expressed, and/or underexpressed for each type of tissue and/or tumor and may be identified for each k cluster as the corresponding genes. In one example, for training a supervised MLA, the annotations provided for each sample would be a full transcriptome gene expression dataset, cancer type, tissue site, and background tissue percentage.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting detection of LOH in a cancer specimen, especially in HLA genes. Embodiments may include a single microservice for executing and delivering HLA LOH detection or may include a plurality of microservices each having a particular role which together implement one or more of the embodiments above. In one example, a first microservice may execute alignment of reads to HLA genes in order to deliver HLA reference sequences to a second microservice for calculating coverage metrics. Similarly, the second microservice may execute calculating coverage metrics to deliver coverage metrics according to an embodiment, above. A third microservice may receive coverage metrics from a second microservice and may execute HLA LOH modeling to deliver an LOH status for each HLA allele in a specimen.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for HLA typing has been received and is ready for processing. The first microservice may execute and notify the order management system once the delivery of HLA typing is ready for the second microservice. Furthermore, the order management system may identify that execution parameters (prerequisites) for the second microservice are satisfied, including that the first microservice has completed, and notify the second microservice that it may continue processing the order to calculate coverage metrics according to an embodiment, above.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. In one example, targeted panels may enable the delivery of next generation sequencing results for HLA LOH detection according to an embodiment, above. An example of the design of next-generation sequencing probes is disclosed, for example, in U.S. Prov. Patent Application No. 62/924,073, titled "Systems and Methods for Next Generation Sequencing Uniform Probe Design", and filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce HLA LOH detection as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT 19/69161, both titled "Transcriptome Deconvolution of Metastatic Tissue Samples", and filed Dec. 31, 2019, U.S. Prov. Patent Application No. 62/924,054, titled "Calculating Cell-type RNA Profiles for Diagnosis and Treatment", and filed Oct. 21, 2019, and U.S. Prov. Patent Application No. 62/944,995, titled "Rapid Deconvolution of Bulk RNA Transcriptomes for Large Data Sets (Including Transcriptomes of Specimens Having Two or More Tissue Types)", and filed Dec. 6, 2019 which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. Prov. Patent Application No. 62/855,750, titled "Systems and Methods for Multi-Label Cancer Classification", and filed May 31, 2019, which is incorporated herein by reference and in its entirety for all purposes. An example of a tumor mutational burden (TMB) engine is disclosed, for example, in U.S. Prov. Patent Application No. 62/804,458, titled "Assessment of Tumor Burden Methodologies for Targeted Panel Sequencing", and filed Feb. 12, 2019, which is incorporated herein by reference and in its entirety for all purposes. An example of a PD-L1 status engine is disclosed, for example, in U.S. Prov. Patent Application No. 62/854,400, titled "A Pan-Cancer Model to Predict The PD-L1 Status of a Cancer Cell Sample Using RNA Expression Data and Other Patient Data", and filed May 30, 2019, which is incorporated herein by reference and in its entirety for all purposes. An additional example of a PD-L1 status engine is disclosed, for example, in U.S. Prov. Patent Application No. 62/824,039, titled "PD-L1 Prediction Using H&E Slide Images", and filed Mar. 26, 2019, which is incorporated herein by reference and in its entirety for all purposes. An example of a homologous recombination deficiency engine is disclosed, for example, in U.S. Prov. Patent Application No. 62/804,730, titled "An Integrative Machine-Learning Framework to Predict Homologous Recombination Deficiency", and filed Feb. 12, 2019, which is incorporated herein by reference and in its entirety for all purposes. An example of a cellular pathway activation report engine is disclosed, for example, in U.S. Prov. Patent Application No. 62/888,163, titled "Cellular Pathway Report", and filed Aug. 16, 2019, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. Prov. Patent Application No. 62/931,600, titled "Systems and Methods for Detecting Microsatellite Instability of a Cancer Using a Liquid Biopsy", and filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944,292, titled "Large Scale Phenotypic Organoid Analysis", filed Dec. 5, 2019, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

What is claimed is:

1. A computer-implemented method of detecting loss of heterozygosity (LOH) of a human leukocyte antigen (HLA) gene in a subject, the method comprising:
   receiving next generation sequencing data generated from a biological sample of the subject;
   aligning the next generation sequencing data against a reference genome to determine a mapped reads dataset and an unmapped reads dataset;
   providing at least the unmapped reads dataset to an HLA typing process to identify at least one candidate HLA allele for the HLA gene;
   identifying a HLA sequence associated with each identified candidate HLA allele;
   creating a HLA reference genome using each identified HLA sequence;
   aligning the next generation sequencing data against the HLA reference genome and adjusting the HLA reference genome to account for a variant identified during the aligning;
   aligning the next generation sequencing data against the adjusted HLA reference genome to determine at least one read depth coverage measures, wherein the at least one read depth coverage measures is associated with a segment of the adjusted HLA reference genome associated with one of the identified candidate HLA alleles;
   providing the at least one read depth coverage measures to a LOH modeling process;
   determining, using the LOH modeling process, a LOH status for the HLA gene; and
   generating and storing a report of the LOH status for the HLA gene.

2. A computer-implemented method of creating a HLA reference genome specific to a subject, the method comprising:
   receiving normal next generation sequencing data generated from a buffy coat preparation of a blood sample of the subject;
   aligning the next generation sequencing data against a reference genome to determine a normal mapped reads dataset and a normal unmapped reads dataset;
   receiving tumor next generation sequencing data generated from a tumor specimen of the subject;
   providing at least a portion of the normal unmapped reads dataset to an HLA typing process to identify at least one candidate HLA allele for the HLA gene;
   identifying a HLA sequence associated with each identified candidate HLA allele; and
   creating a HLA reference genome using each identified HLA sequence.

3. A computer-implemented method of detecting loss of heterozygosity (LOH) of a human leukocyte antigen (HLA) gene in a subject, the method comprising:
   receiving normal next generation sequencing data generated from a buffy coat preparation of a blood sample of the subject;
   aligning the next generation sequencing data against a reference genome to determine a normal mapped reads dataset and a normal unmapped reads dataset;
   receiving tumor next generation sequencing data generated from a tumor specimen of the subject;
   providing at least a portion of the normal unmapped reads dataset to an HLA typing process to identify at least one candidate HLA allele for the HLA gene;
   identifying a HLA sequence associated with each identified candidate HLA allele;

creating a HLA reference genome using each identified HLA sequence;

aligning the normal next generation sequencing dataset against the HLA reference genome and adjusting the HLA reference genome to account for a variant identified during the aligning;

aligning the normal next generation sequencing dataset against the adjusted HLA reference genome to determine at least one normal read depth coverage measures, wherein the at least one normal read depth coverage measures is associated with a segment of the adjusted HLA reference genome associated with one of the identified candidate HLA alleles;

aligning the tumor next generation sequencing dataset against the adjusted HLA reference genome to determine at least one tumor read depth coverage measures, wherein the at least one tumor read depth coverage measures is associated with a segment of the adjusted HLA reference genome associated with one of the identified candidate HLA alleles;

providing the at least one normal read depth coverage measures and the at least one tumor read depth coverage measures to a LOH modeling process;

determining, using the LOH modeling process, a LOH status for the HLA gene; and generating and storing a report of the LOH status for the HLA gene.

4. The method of claim 3, wherein determining the LOH status for the HLA gene comprises applying a shallow decision tree model to the received read depth coverage measures.

5. The method of claim 3, wherein determining the LOH status for each HLA gene comprises applying a random forest model to the received read depth coverage measures.

6. The method of claim 3, wherein the next generation sequencing data is generated using short read sequencing.

7. The method of claim 3, wherein the HLA gene is the HLA-A gene.

8. A method for determining loss of heterozygosity for the HLA-A, HLA-B, and HLA-C genes using, for each gene, the method of claim 3.

9. A method for determining loss of heterozygosity for the HLA-E, HLA-F, and HLA-G genes using, for each gene, the method of claim 3.

10. A method for determining loss of heterozygosity for the DRA, DRB1, DQA1, DQB1, DPA1, and DPB1 genes using, for each gene, the method of claim 3.

11. The method of claim 3, wherein at least a portion of the reads data comprises forward reads from paired-end reads.

12. The method of claim 3, wherein determining the LOH status for the HLA gene comprises determining the LOH status is a loss of heterozygosity when a read depth coverage measure is below a threshold.

13. The method of claim 3, wherein determining the LOH status for the HLA gene comprises determining the LOH status is a stable status when a read depth coverage measure is above a threshold.

14. The method of claim 3, wherein the HLA typing process applies an Optitype HLA typing algorithm.

15. The method of claim 3, wherein the HLA typing process applies a Kourami HLA typing algorithm.

16. The method of claim 3, wherein the HLA reference genome further comprises at least one HLA pseudogene sequence.

17. The method of claim 3, wherein the step of providing at least a portion of the normal unmapped reads dataset to the HLA typing process to identify at least one candidate HLA allele for the HLA gene comprises providing at least a portion of the normal unmapped reads dataset and a portion of the normal mapped reads dataset to the HLA typing process.

18. The method of claim 3, wherein the step of aligning the tumor next generation sequencing dataset against the adjusted HLA reference genome to determine at least one tumor read depth coverage measures comprises filtering the tumor next generation sequencing dataset.

19. The method of claim 18, wherein the step of filtering the tumor next generation sequencing dataset comprises removing reads that are not properly aligned.

20. The method of claim 18, wherein the step of filtering the tumor next generation sequencing dataset comprises removing duplicate reads.

21. The method of claim 18, wherein the step of filtering the tumor next generation sequencing dataset comprises removing a read based on an edit distance associated with the read.

22. The method of claim 3, wherein the tumor specimen is a solid tumor specimen.

23. The method of claim 3, wherein the tumor specimen is a cell free DNA (cfDNA) specimen.

24. The method of claim 3, wherein the tumor specimen is a lung tumor specimen.

25. The method of claim 3, wherein the tumor specimen is a metastatic specimen.

26. The method of claim 3, wherein the tumor specimen is a colorectal specimen.

27. The method of claim 3, wherein the method is implemented on one or more microservices.

28. The method of claim 3, wherein the method further comprises:
    when it is determined that the cancer in the subject does not have a loss of heterozygosity in the HLA gene, treating the cancer by administering a checkpoint inhibitor therapy to the subject.

29. The method of claim 28, wherein the checkpoint inhibitor therapy is selected from the group consisting of an anti-CTLA-4 therapy, an anti-PD-1 therapy, or an anti-PD-L1 therapy.

30. The method of claim 1, wherein the biological sample is selected from the group consisting of a tumor specimen or a buffy coat preparation.

* * * * *